United States Patent
Harmelin et al.

(10) Patent No.: US 11,540,725 B2
(45) Date of Patent: Jan. 3, 2023

(54) SYSTEMS AND METHODS FOR GENERATING 3D IMAGES BASED ON FLUORESCENT ILLUMINATION

(71) Applicant: Yeda Research and Development Co. Ltd., Rehovot (IL)

(72) Inventors: Alon Harmelin, Rishpon (IL); Vyacheslav Kalchenko, Rehovot (IL); Guillaume Molodij, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 857 days.

(21) Appl. No.: 16/334,037

(22) PCT Filed: Sep. 12, 2017

(86) PCT No.: PCT/IL2017/051024
§ 371 (c)(1),
(2) Date: Mar. 18, 2019

(87) PCT Pub. No.: WO2018/051336
PCT Pub. Date: Mar. 22, 2018

(65) Prior Publication Data
US 2019/0254535 A1   Aug. 22, 2019

Related U.S. Application Data

(60) Provisional application No. 62/396,163, filed on Sep. 18, 2016.

(51) Int. Cl.
*A61B 5/02* (2006.01)
*G06T 7/593* (2017.01)
(Continued)

(52) U.S. Cl.
CPC ........ *A61B 5/02007* (2013.01); *A61B 5/0071* (2013.01); *A61B 5/0073* (2013.01);
(Continued)

(58) Field of Classification Search
CPC . A61B 5/02007; A61B 5/0071; A61B 5/0073; A61B 5/0077; A61B 5/7267;
(Continued)

(56) References Cited

U.S. PATENT DOCUMENTS 6,198,852 B1 * 3/2001 Anandan .............. G06V 10/147
                                                              382/284
6,366,638 B1 * 4/2002 Hsieh ...................... A61B 6/488
                                                               378/19

(Continued)

FOREIGN PATENT DOCUMENTS

JP   2006-039658   2/2006
JP   2010-054356   3/2010
(Continued)

OTHER PUBLICATIONS

Molodij et al. "Enhancing retinal images by extracting structural information", 2014, Optics Communications, 313, 321-328 (Year: 2014).*

(Continued)

*Primary Examiner* — Joseph M Santos Rodriguez
*Assistant Examiner* — Kaitlyn E Sebastian

(57) ABSTRACT

There is provided a computer implemented method for generating a three dimensional (3D) image based of fluorescent illumination, comprising: receiving in parallel by each of at least three imaging sensors positioned at a respective parallax towards an object having a plurality of regions with fluorescent illumination therein, a respective sequence of a plurality of images including fluorescent illumination of the plurality of regions, each of the plurality of images separated by an interval of time; analyzing the respective sequences, to create a volume-dataset indicative (Continued)

of the depth of each respective region of the plurality of regions; and generating a 3D image according to the volume-dataset.

21 Claims, 17 Drawing Sheets

(51) Int. Cl.
```
    G06T 7/246      (2017.01)
    G06T 5/00       (2006.01)
    G06T 5/20       (2006.01)
    A61B 5/00       (2006.01)
    G06T 7/55       (2017.01)
```
(52) U.S. Cl.
CPC .......... *A61B 5/0077* (2013.01); *A61B 5/7267* (2013.01); *G06T 5/002* (2013.01); *G06T 5/20* (2013.01); *G06T 7/246* (2017.01); *G06T 7/55* (2017.01); *G06T 7/596* (2017.01); *G06T 2207/10012* (2013.01); *G06T 2207/10021* (2013.01); *G06T 2207/10064* (2013.01); *G06T 2207/20084* (2013.01); *G06T 2207/20088* (2013.01); *G06T 2207/30101* (2013.01)

(58) Field of Classification Search
CPC ........... G06T 5/002; G06T 5/20; G06T 7/246; G06T 7/55; G06T 7/596; G06T 2207/10012; G06T 2207/10021; G06T 2207/10064; G06T 2207/20084; G06T 2207/20088; G06T 2207/30101
See application file for complete search history.

(56) References Cited

U.S. PATENT DOCUMENTS

| | | | |
|---|---|---|---|
| 2006/0039658 | A1 | 2/2006 | Tsukahara et al. |
| 2009/0016587 | A1* | 1/2009 | Strobel ............... G06T 7/20 382/130 |
| 2011/0157373 | A1 | 6/2011 | Ye et al. |
| 2012/0200748 | A1* | 8/2012 | Utsugi ............ H04N 5/213 348/241 |
| 2013/0184570 | A1* | 7/2013 | Wang ............ G06T 7/12 600/425 |
| 2013/0304405 | A1* | 11/2013 | Schmid .......... A61B 5/14542 702/56 |
| 2014/0039309 | A1 | 2/2014 | Harris et al. |
| 2014/0276008 | A1* | 9/2014 | Steinbach ........ A61B 5/0059 600/424 |
| 2015/0015692 | A1* | 1/2015 | Smart ............ G06T 7/337 348/77 |
| 2016/0157725 | A1 | 6/2016 | Munoz |
| 2017/0345130 | A1* | 11/2017 | Wang ............ H04N 19/172 |
| 2018/0061059 | A1* | 3/2018 | Xu ............... G06T 7/0012 |

FOREIGN PATENT DOCUMENTS

| | | |
|---|---|---|
| JP | 2013-515959 | 5/2013 |
| WO | WO 2015/166503 | 11/2015 |
| WO | WO 2018/051336 | 3/2018 |

OTHER PUBLICATIONS

Notice of Reasons for Rejection dated Apr. 12, 2022 From the Japan Patent Office Re. Application No. 2019-514265 together with its Translation into English.. (7 Pages).
International Preliminary Report on Patentability dated Mar. 28, 2019 From the International Bureau of WIPO Re. Application No. PCT/IL2017/051024. (9 Pages).
International Search Report and the Written Opinion dated Dec. 5, 2017 From the International Searching Authority Re. Application No. PCT/IL2017/051024. (13 Pages).
Andrews et al. "PDF Models for Uplink to Space in the Presence of Beam Wander", Proceedings of the SPIE, 6551: 655109-1-655109-12, Apr. 27, 2007.
Brecher "Should Astronomy Abolish Magnitudes?", 199th Meeting of the American Astronomical Society, Washington, DC, USA, Bulletin of the American Astronomical Society, 33: 1363, # 40.02, Dec. 2001.
Bronstein et al. "Quasi-Maximum Likelihood Blind Deconvolution of Images Acquired Through Scattering Media", 2004 IEEE International Symposium on Biomedical Imaging: Nano to Macro, Arlington, VA, USA, Apr. 18, 2004. 4 P., Apr. 18, 2004.
Hill et al. "Probability Distribution of Irradiance for the Onset of Strong Scintillation", Journal of the Optical Society of America A, JOSAA, 14(7): 1530-1540, Jul. 1997.
Johnson et al. "Ultra-High Resolution Intensity Statistics of A Scintillating Source", The Astrophysical Journal, 755: 179-1-179-12, Aug. 7, 2012.
Kalchenko et al. "A Simple Approach for Non-Invasive Transcranial Optical Vascular Imaging (nTOVI)", Journal of Biophotonics, p. 1-5, First Published Online Apr. 29, 2015.
Kalchenko et al. "Combined Application of Dynamic Light Scattering Imaging and Fluorescence Intravital Microscopy in Vascular Biology", Laser Physics Letters, 7(8): 603-606, Published Online Jun. 1, 2010.
Kalchenko et al. "In Vivo Characterization of Tumor and Tumor Vascular Network Using Multi-Modal Imaging Approach", Journal of Biophotonics. 4(9): 645-649. Sep. 1, 2011.
Kalchenko et al. "Label Free In Vivo Laser Speckle Imaging of Blood and Lymph Vessels", Journal of Biomedical Optics, 17(5): 050502-1-050502-3, Published Online May 4, 2012.
Kalchenko et al. "Transcranial Optical Vascular Imaging (TOVI) of Cortical Hemodynamics in Mouse Brain", Scientific Reports, 4(5839): 1-7, Jul. 25, 2014.
Molodij et al. "A Method for Single Image Restoration Based on the Principal Ergodic", Journal of the Optical Society of America A: Optics, Image Science, and Vision, 27(11): 2459-2467, Nov. 2010.
Molodij et al. "Enhancing Retinal Images by Extracting Structural Information", Optics Communications, 313: 321-328, Available Online Oct. 22, 2013.
Molodij et al. "Enhancing Retinal Images by Nonlinear Registration", Optics Communications, 342: 157-166, May 1, 2015.
Murez et al. "Photometric Stereo in a Scattering Medium", Proceedings of the International Conference on Computer Vision, ICCV 2015, Santiago, Chile, Dec. 7-13, 2015, p. 3415-3423, Dec. 7, 2015.
Nandy et al. "Shape From Recognition: A Novel Approach for 3-D Face Shape Recovery", IEEE Transactions on Image Processing, 10(2): 206-217, Feb. 2001.
Romdhani et al. "Estimating 3D Shape and Texture Using Pixel Intensity, Edges, Specular Highlights, Texture Constraints and a Prior", Proceedings of the IEEE Computer Society Conference on Computer Vision and Pattern Recognition, VCPR'05, San Diego, CA, USA, Jun. 20-25, 2005, 2: 986-993, Jun. 20, 2005.
Sato et al. "Bispectral Photometric Stereo Based on Fluorescence", Proceedings of the 2012 IEEE Conference on Computer Vision and Pattern Recognition, CVPR'12, Providence, RI, USA, Jun. 16-21, 2012, p. 270-277, Jun. 16, 2012.
Seo et al. "Principal Component Analysis of Dynamic Fluorescence Images for Diagnosis of Diabetic Vasculopathy", Journal of Biomedical Optics, 21(4):046003-1-046003-9, Apr. 2016.
Song et al. "Three-Dimensional Face Reconstruction From a Single Image by a Coupled RBF Network", IEEE Transactions on Image Processing, 21(5): 2887-2897, Published Online Apr. 18, 2012.
Tatarskii "The Effects of the Turbulent Athmosphere on Wave Propagation", Israel Program for Scientific Translations, Povided by the NASA Astrophysics Data System, Chap.1-5: 1-472, 1971.
Treibitz et al. "Shape From Fluorescence", Proceedings of the 12th European Conference on Computer Vision—Part VII, ECCV 2012, Florence, Italy, Oct. 7-13, 2012, LNCS 7578: 292-306, Oct. 7, 2012.
Zbontar et al. "Computing the Stereo Matching Cost With a Convolutional Neural Network", Proceedings of the 2015 IEE Conference on Computer Vision and Pattern Recognition, CVPR, Jun. 7-12, 2015, p. 1592-1599, Jun. 2015.

(56) References Cited

OTHER PUBLICATIONS

Notice of Reason(s) for Rejection dated Sep. 2, 2021 From the Japan Patent Office Re. Application No. 2019-514265 and Its Translation Into English. (8 Pages).

* cited by examiner

SYSTEMS AND METHODS FOR GENERATING 3D IMAGES BASED ON FLUORESCENT ILLUMINATION

RELATED APPLICATIONS

This application is a National Phase of PCT Patent Application No. PCT/IL2017/051024 having International filing date of Sep. 12, 2017, which claims the benefit of priority under 35 USC § 119(e) of U.S. Provisional Patent Application No. 62/396,163 filed on Sep. 18, 2016. The contents of the above applications are all incorporated by reference as if fully set forth herein in their entirety.

BACKGROUND

The present invention, in some embodiments thereof, relates to fluorescent imaging and, more specifically, but not exclusively, to systems and methods for generating a 3D image based on fluorescent illumination agent(s).

Imaging based on fluorescent illumination is used, for example, to perform imaging of cerebral blood vessels in clinical and preclinical practice. Fluorescent illumination based imaging may generate non-invasive or minimally invasive images, for example, of blood vessels.

An exemplary method of in vivo optical imaging, intravital microscopy, is an essential tool that advances knowledge of how intact biological organisms work. Intravital microscopy is a powerful tool, providing the ability to characterize live organism physiology in the natural context of cellular and sub cellular resolution. However, the small field of view and the use of highly expensive and complicated equipment limit the usefulness of intravital imaging in general biological research. Standard or advanced intravital microscopy is useful when the field of view (FOV) does not extend 2 millimeters (mm) and the depth does not extend a few hundred microns.

Another exemplary method based on fluorescent imaging, termed trans-cranial optical vessel imaging (TOVI), is invented by the same inventors of the current application. The method is based on the administration of fluorescent contrast material into circulation. The method generates 2D images. Using TOVI, cerebral blood vessels may be observed at a FOV of 15 mm through the intact cranium and intact skin.

SUMMARY

According to a first aspect, a computer implemented method of generating a three dimensional (3D) image based on fluorescent illumination, comprises: receiving in parallel by each of at least three imaging sensors positioned at a respective parallax towards an object having a plurality of regions with fluorescent illumination therein, a respective sequence of a plurality of images including fluorescent illumination of the plurality of regions, each of the plurality of images separated by an interval of time, analyzing the respective sequences, to create a volume-dataset indicative of the depth of each respective region of the plurality of regions, and generating a 3D image according to the volume-dataset.

According to a second aspect, a system for generating a three dimensional (3D) image based on fluorescent illumination, comprises: an imaging interface that receives in parallel by each of at least three imaging sensors positioned at a respective parallax towards an object having a plurality of regions with fluorescent illumination therein, a respective sequence of a plurality of images including fluorescent illumination of the plurality of regions, each of the plurality of images separated by an interval of time, a program store storing code, and at least one processor coupled to the imaging interface and the program store for implementing the stored code, the code comprising: code to analyze the respective sequences, create a volume-dataset indicative of the depth of each respective region of the plurality of regions, and generate a 3D image according to the volume-dataset.

According to a third aspect, a computer program product comprising a non-transitory computer readable storage medium storing program code thereon for implementation by at least one processor, for generating a three dimensional (3D) image based on fluorescent illumination, comprises: code instructions to receive in parallel by each of at least three imaging sensors positioned at a respective parallax towards an object having a plurality of regions with fluorescent illumination therein, a respective sequence of a plurality of images including fluorescent illumination of the plurality of regions, each of the plurality of images separated by an interval of time, code instructions to analyze the respective sequences, to create a volume-dataset indicative of the depth of each respective region of the plurality of regions, and code instructions to generate a 3D image according to the volume-dataset.

The systems and/or methods (e.g., code instructions stored in a storage device executed by processor(s)) provided herein provide a technical solution to the technical problem of improving the accuracy and/or resolution of the imaging of fluorescent illuminated regions of an object. The technical problem may relate to (optionally non-invasive) intravital imaging of blood vessels and/or lumens within the living mammal (e.g., human, mouse, pig, sheep, dog, rabbit, cat). The technical problem may relate to classification of the types of the blood vessels and/or lumens according to the fluorescent illuminated regions. The technical problem may relate to resolving structural details, for example, differentiating between arteries and veins, and/or differentiating between a vessel bifurcation and two vessels crossing over each other. The technical problem may relate to improving the accuracy and/or resolution of the location of the blood vessels and/or lumens in the generated 3D image based on the fluorescent illuminated regions.

The systems and/or methods (e.g., code instructions stored in a storage device executed by processor(s)) provided herein provide a technical solution to the technical problem of scattering (i.e., of the fluorescent light by the medium) and/or absorption of light in living tissues during in vivo optical imaging. The scattering and/or absorption of light limit the ability to image structures and/or obtain functional information deep inside tissues at a high enough resolution that is clinically significant. The systems and/or methods provided herein improve spatial resolution and/or extend the depth of imaging based on fluorescent illumination agent during in vivo optical imaging. The systems and/or methods provided herein resolve otherwise hidden structural and/or functional details in the 3D images obtained from living subjects. Such dynamic details cannot be obtained using other standard imaging methods, for example, magnetic resonance imaging.

The systems and/or methods (e.g., code instructions stored in a storage device executed by processor(s)) described herein improve performance of a computing unit of an intravital imaging system that creates images using imaging sensors that capture fluorescent illumination of agent(s) administered to the living mammal. The improvement in performance includes at least improved accuracy and/or resolution of the generated 3D image, including identifying of the type of vessel(s) and/or lumen(s) captured by the imaging sensors based on the fluorescent illumination. The improvement in performance may include generation of the 3D image using less memory, and/or using fewer computational resources (e.g., processor(s) utilization), and/or faster computation time, without sacrificing the quality of the resulting image.

In a further implementation form of the first, second, and third aspects, the object includes tissue within a living mammal, the fluorescent illuminated regions include a plurality of blood vessels injected with fluorescent illumination agent located below the skin of the living mammal, and the at least three imaging sensors are located externally to the skin and non-contacting the skin.

In a further implementation form of the first, second, and third aspects, the analyzing comprises analyzing the respective sequences to compute a respective parallax-dataset for each pair of imaging sensors of the at least three imaging sensors, and computing the volume-dataset based on the respective parallax-dataset of each pair of imaging sensors, wherein the volume-dataset is indicative of the 3D location of each region of the plurality of regions.

In a further implementation form of the first, second, and third aspects, the analyzing comprises computing a time similarity index based on an analysis of at least one pattern indicative of a change of the intensity of the fluorescent illumination at respective image elements of each respective sequence, and computing a type of each of the regions according to the time similarity index.

In a further implementation form of the first, second, and third aspects, the type of each of the regions is computed by linking image elements having a similarity of the at least one pattern indicative of the change of intensity of the fluorescent illumination, wherein the similarity is defined according to a similarity requirement based on the time similarity index.

In a further implementation form of the first, second, and third aspects, the similarity requirement is computed according to the equation:

$$S_i = \left[ \frac{\text{Max}[I_r^2(t)]}{\delta_d} \right]^{1/3}$$

Where: Ir(t) denotes a reference temporal function, Si denotes a temporal assessment that defines relative distance between Ic(t) denoting a current temporal function, by comparison with Ir(t), $$\delta_d = \sum_{t=0}^{T} \frac{|I_c(t) - I_r(t)|}{I_c(t) + I_r(t)},$$

and the similarity is computed as a Manhattan distance according to the relationship |Ic(t)-Ir(t)|.

In a further implementation form of the first, second, and third aspects, the at least one pattern indicative of the change in the intensity of the fluorescent illumination comprises time to maximum intensity of the fluorescent illumination.

In a further implementation form of the first, second, and third aspects, the at least one pattern indicative of the change in the intensity of the fluorescent illumination comprises approximately stable intensity of the fluorescent illumination over a time interval.

In a further implementation form of the first, second, and third aspects, the type is selected from the group consisting of: a bifurcation of a blood vessel, a first blood vessel at a higher tissue level crossing over a second blood vessel at a lower tissue level, an artery, a vein, a lymphatic vessel, cerebrospinal fluid (CSF) containing lumen, an air filled lumen associated with the digestive system, and a urine filled lumen associated with the urinary system.

In a further implementation form of the first, second, and third aspects, the method further comprises and/or the system further includes code for and/or the computer program product includes additional instructions for associating each region of the plurality of regions defined by the volume-dataset with at least one visual marker indicative of the computed type of each respective region of the plurality of regions, and wherein generating the 3D image comprises generating the 3D image based on the at least one visual marker.

In a further implementation form of the first, second, and third aspects, a neural network receives the respective sequences and computes the time similarity index, to output the volume-dataset indicative of the depth of each respective region of the plurality of regions.

In a further implementation form of the first, second, and third aspects, the method further comprises and/or the system further includes code for and/or the computer program product includes additional instructions for calculating an isotropic reference, and improving spatial resolution of the generated 3D image according to the isotropic reference.

In a further implementation form of the first, second, and third aspects, the method further comprises and/or the system further includes code for and/or the computer program product includes additional instructions for calculating a spatio-temporal distortion compensation matrix (STDCM) that includes weighted coefficients, and applying the STDCM to the volume-dataset to correct the depth coordinates of each image element of each region.

In a further implementation form of the first, second, and third aspects, the STDCM is computed based on a plurality of computed time shape index parameters associated with at least one pattern of fluorescent intensity over time at each respective image element, computed based on the respective sequences, wherein the plurality of computed time shape index parameters are used to resolve structure and/or function details of the volume-dataset.

In a further implementation form of the first, second, and third aspects, the plurality of computed time shape index parameters used to resolve structure and/or function details are selected from the group consisting of: fine structural details, type of blood vessel, topology indicating a bifurcation of a vessel or crossing over of vessels, blood vessel classification, fluorescent contrast extravasation, and normal functional state or abnormal behavior.

In a further implementation form of the first, second, and third aspects, the method further comprises and/or the system further includes code for and/or the computer program product includes additional instructions for calculating a motion estimator based on an analysis of changes in intensity of the fluorescent illumination of the image elements of the respective sequences, and applying the motion estimator to the volume-dataset to correct motion artifacts.

In a further implementation form of the first, second, and third aspects, the method further comprises and/or the system further includes code for and/or the computer program product includes additional instructions for computing a deconvolution parameter that compensates for scattering of the fluorescent illumination and estimates diffusion of the fluorescent illumination agent leaking out of vessels, the deconvolution parameter used to correct the volume-dataset and improve spatial resolution of the plurality of regions.

In a further implementation form of the first, second, and third aspects, the method further comprises and/or the system further includes code for and/or the computer program product includes additional instructions for computing structure tensors based on the respective parallax shift of at least three imaging sensors, and computing the volume-dataset according to the structure tensors for improving the depth and/or parallax sensitivity of the plurality of regions within the 3D image.

In a further implementation form of the first, second, and third aspects, the analyzing the respective sequences is performed using a trained time similarity index classifier that receives as input a computed initial location of each respective image element according to respective sequences of the at least three image sensors, and at least one pattern of changes in fluorescent imaging at each respective image element, and outputs the volume-dataset based on a computed maximum correlation of the location of each respective image element.

In a further implementation form of the first, second, and third aspects, the method further comprises and/or the system further includes code for and/or the computer program product includes additional instructions for applying an adaptive filter to each respective sequence received by each of the at least three image sensors, the adaptive filter designed to improve spatial resolution of the location of each region and reduce noise during variations in intensity of the fluorescent illumination.

In a further implementation form of the first, second, and third aspects, the method further comprises and/or the system further includes code for and/or the computer program product includes additional instructions for applying an adaptive filter to each respective sequence received by each of the at least three image sensors, the adaptive filter designed to remove scattering effect of media of the object, wherein the adaptive filter is implemented as a super-Gaussian background subtraction by subtracting the adaptive filter from each image of the plurality of image of each sequence.

In a further implementation form of the first, second, and third aspects, the method further comprises operating and/or the system further comprises for and/or the computer program product includes additional instructions for operating a laser and another imaging sensor positioned at the center of the at least three imaging sensors, and code instructions stored by the program store, the code comprising code to analyze the images created based on reflections of the laser captured by the another imaging sensor to compute laser speckle imaging (LSI), and generate the 3D image in real-time based on the volume-dataset using the LSI as an independent reference.

In a further implementation form of the first, second, and third aspects, the LSI is used to determine a 3D flow map of blood vessels.

In a further implementation form of the first, second, and third aspects, the LSI is used to correct 3D coordinates of the regions of the volume-dataset.

In a further implementation form of the first, second, and third aspects, the at least three imaging sensors are positioned at the same z axis value of an x-y-z space.

In a further implementation form of the first, second, and third aspects, the at least three imaging sensors include a complementary metal oxide semiconductor (CMOS) sensor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
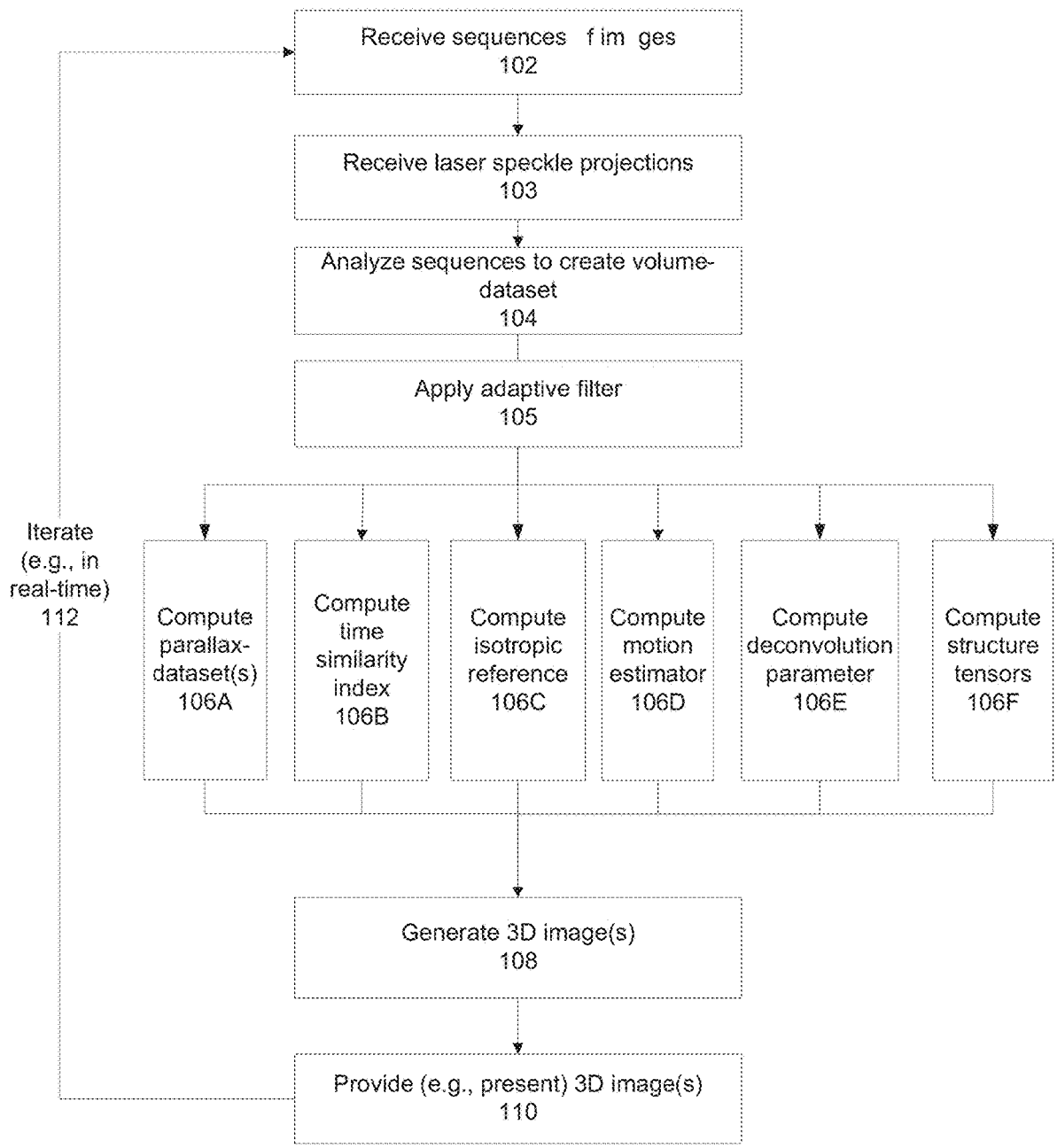
FIG. 1 is flowchart of a method for generating a 3D image of regions of an object based on fluorescent illumination from within the regions acquired using a sequence of time spaced images using at least three imaging sensors, in accordance with some embodiments of the present invention.

The present invention, in some embodiments thereof, relates to fluorescent imaging and, more specifically, but not exclusively, to systems and methods for generating a 3D image based on fluorescent illumination.

An aspect of some embodiments of the present invention relates to systems and/or methods (e.g., code instructions stored in a storage device executed by processor(s)) that generate a 3D image(s) based on volume-dataset(s) created based on an analysis of sequences of time spaced images (e.g., time stamped), each respective sequence acquired by one of three (or more) image sensors positioned non-parallel (i.e., having a respective parallax) towards an object having fluorescent illuminated regions. The 3D image, based on the fluorescent illuminated regions, provides structural and/or functional details of the object, optionally of otherwise hidden regions. Optical trans-skin imaging may be performed. For example, the 3D image may be performed non-invasively, to image blood vessels of a subject (e.g., human, animal), optionally in real-time, for example, imaging of the blood vessels of the brain of a human or mouse to evaluate the effects of a stroke, identify a tumor, or other applications. In the case of trans-skin imaging of organisms (e.g., mammals), the fluorescent illuminated regions (e.g., blood vessels) are located below the skin of the living mammal, and the three (or more) imaging sensors are located externally to the skin of the living animal. The three (or more) imaging sensors are non-contacting the skin (i.e., spaced apart from the skin of the living mammal). The images captured by the imaging sensors are based on fluorescence light that traversed the skin (and other tissues) and were affected by the skin (and other tissues), for example, scattering as described herein.

Optionally, parallax-datasets are computed for each pair of the imaging sensors based on the captured sequences, for example, three parallax-datasets are computed for the three combinations of pairs when three imaging sensors are used. The volume-dataset is computed based on the parallax-datasets, for example, using a trained statistical classifier, and/or (optionally convolutional) neural network. The 3D image is generated based on the volume-dataset.

Alternatively or additionally, the volume-dataset is generated based on an analysis of fluorescent illumination pattern(s) of the sequences. The patterns are indicative of changes of the intensity of fluorescent illumination over the time spaced images of each sequence. Patterns may be computed per image element (e.g., pixel, voxel) and/or group of image elements. The patterns may be represented as a temporal function indicative of the change of intensity over time.

Optionally, the pattern is indicative of the time to reach maximum intensity of the fluorescent illumination. Alternatively or additionally, the pattern is indicative of stability of the intensity of the fluorescent illumination. Image elements having similar patterns (e.g., according to a similarity requirement, for example, a statistical distance and/or correlation) may be grouped together. The grouped image elements may be identified as one or more predefined types indicative of structure and/or function, and/or may be used to resolve structural detail, for example, to differentiate between arteries and veins, and/or to differentiate between a bifurcation of a vessel and two vessels crossing over one another.

The systems and/or methods (e.g., code instructions stored in a storage device executed by processor(s)) provided herein provide a technical solution to the technical problem of improving the accuracy and/or resolution of the imaging of fluorescent illuminated regions of an object. The technical problem may relate to (optionally non-invasive) intravital imaging of blood vessels and/or lumens within the living mammal (e.g., human, mouse, pig, sheep, dog, rabbit, cat). The technical problem may relate to classification of the types of the blood vessels and/or lumens according to the fluorescent illuminated regions. The technical problem may relate to resolving structural details, for example, differentiating between arteries and veins, and/or differentiating between a vessel bifurcation and two vessels crossing over each other. The technical problem may relate to improving the accuracy and/or resolution of the location of the blood vessels and/or lumens in the generated 3D image based on the fluorescent illuminated regions.

The systems and/or methods (e.g., code instructions stored in a storage device executed by processor(s)) provided herein provide a technical solution to the technical problem of scattering (i.e., of the fluorescent light by the medium) and/or absorption of light in living tissues during in vivo optical imaging. The scattering and/or absorption of light limit the ability to image structures and/or obtain functional information deep inside tissues at a high enough resolution that is clinically significant. The systems and/or methods provided herein improve spatial resolution and/or extend the depth of imaging based on fluorescent illumination agent during in vivo optical imaging. The systems and/or methods provided herein resolve otherwise hidden structural and/or functional details in the 3D images obtained from living subjects. Such dynamic details cannot be obtained using other standard imaging methods, for example, magnetic resonance imaging.

It is noted that the systems and/or methods (e.g., code instructions executed by processor(s)) that identify the type and/or location of image elements and/or regions based on an analysis of patterns of fluorescent imaging over time (i.e., over multiple sequential images) provide an improvement in computational efficiency over other methods, for example, in comparison with a method based on principal component analysis (PCA), for example, as described with reference to J. Seo, Y. An, J. Lee, T. Ku, Y. Kang, C. Ahn, C. Choi, "Principal component analysis of dynamic fluorescence images for diagnosis of diabetic vasculopathy," J. Biomed. Opt. 21(4), 046003, 2016, incorporated herein in its entirety. The PCA method appears to extract only the principal components using a statistical approach, for example, Seo et al. appear to determine the principal frequent patterns (i.e., temporal behavior modes). In contrast, the systems and/or methods (e.g., code instructions executed by processor(s)) described herein link image elements (e.g., pixels, voxels) that have similar patterns (i.e., temporal behavior) according to a similarity requirement that is based for example, on flow-time delay of the administered fluorescent agent, for example, in the circulatory system. The systems and/or methods (e.g., code instructions executed by processor(s)) described herein are able to detect the more frequent and/or usual patterns (e.g., major arteries, such as in the brain) as well as detecting otherwise hidden abnormalities (e.g., slow leakage of blood out of brain vessels due to a hemorrhagic stroke, and/or abnormal blood vessel angiogenesis in a tumor).

The systems and/or methods (e.g., code instructions stored in a storage device executed by processor(s)) described herein improve performance of a computing unit of an intravital imaging system that creates images using imaging sensors that capture fluorescent illumination of agent(s) administered to the living mammal. The improvement in performance includes at least improved accuracy and/or resolution of the generated 3D image, including identifying of the type of vessel(s) and/or lumen(s) captured by the imaging sensors based on the fluorescent illumination. The improvement in performance may include generation of the 3D image using less memory, and/or using fewer computational resources (e.g., processor(s) utilization), and/or faster computation time, without sacrificing the quality of the resulting image.

The systems and/or methods (e.g., code instructions stored in a storage device executed by processor(s)) provided herein improve an underlying technical process within the technical field of image processing, in particular, within the field of generating 3D images (optionally medical images) based on the administration of fluorescent illuminating agent(s) to an object. The systems and/or methods described herein, generate improved 3D images of regions of the object (e.g., blood vessels within the brain), by revealing fine 3D structural details of the blood vessels, revealing hidden details of the blood vessels (e.g., differentiating between bifurcating blood vessels and blood vessels that cross over one another), resolve depth data, improve light scattering, and reduce or eliminate motion artifacts.

The systems and/or methods (e.g., code instructions executed by one or more processors) described herein are tied to physical real-life components, for example, imaging sensors that each capture a sequence of images based on fluorescent illumination agent(s) administered to region(s) of an object.

Accordingly, the systems and/or methods described herein are inextricably tied to computed technology and/or physical components (i.e., imaging sensors) to overcome an actual technical problem arising in 3D imaging of objects (optionally intravital imaging of a mammal) based on fluorescent illuminating agent(s) administered to the object.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term 3-Y imaging sensor setup (or 3-Y setup) refers to the exemplary positioning of imaging sensors relative to the object, as described herein.

As used herein, the term parallax means the way an object's position or direction seems to change depending on the viewing angle. Each imaging sensor generates a different parallax of the regions with the object. It is noted that the parallax-dataset referred to herein is different than the term parallax used alone, as the parallax-dataset is computed from sequences acquired by a pair of imaging sensors from the multiple (optionally three) imaging sensors.

Figure 2:
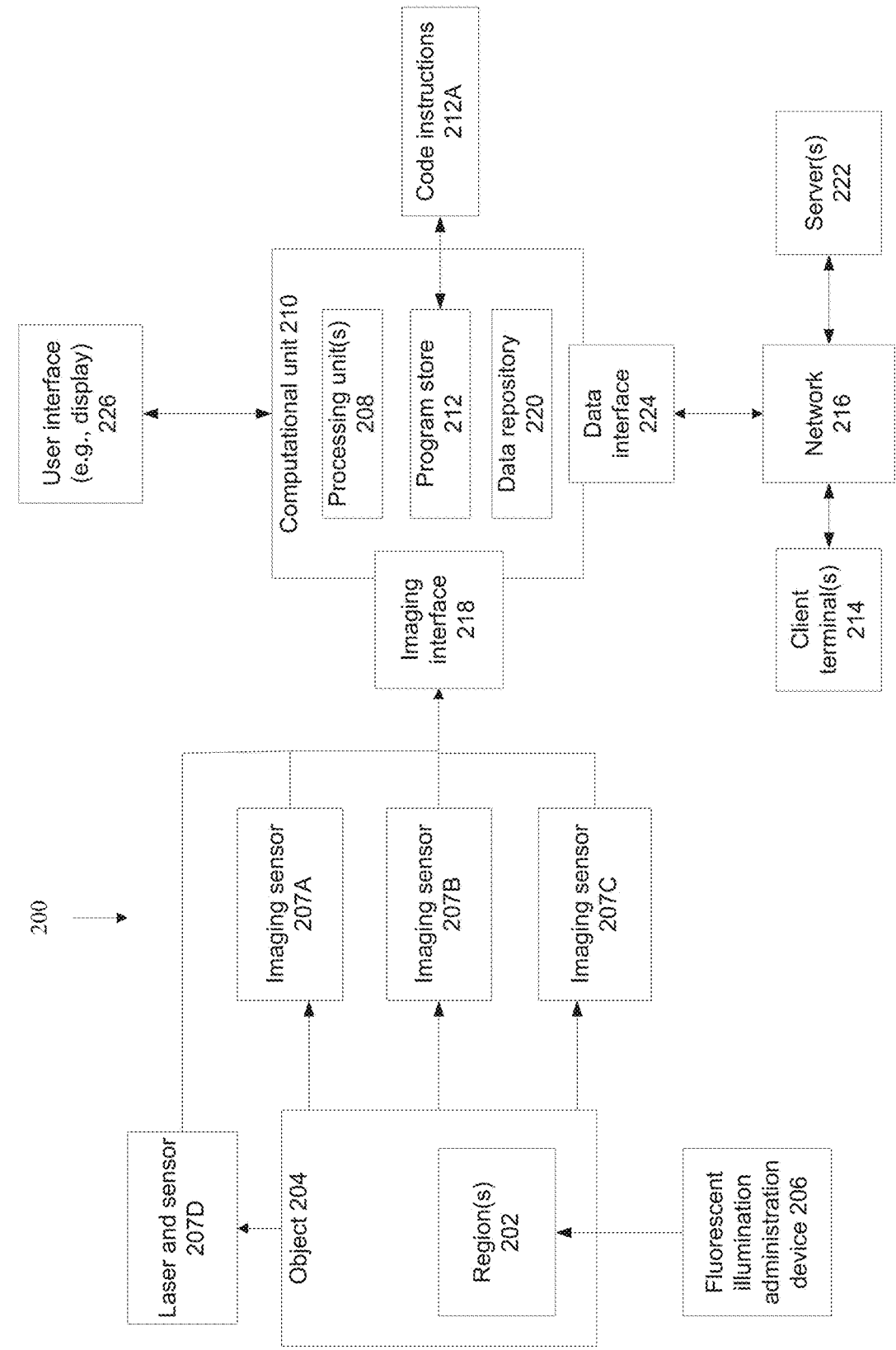
FIG. 2 is a block diagram of components of a system that generates the 3D image of regions of an object based on fluorescent illumination imaged using a sequence of time spaced images captured by at least three imaging sensors, in accordance with some embodiments of the present invention.

Reference is now made to FIG. 1, which is a flowchart of a method for generating a 3D image of regions of an object based on fluorescent illumination from within the regions acquired using a sequence of time spaced images using at least three imaging sensors, in accordance with some embodiments of the present invention. Reference is also made to FIG. 2, which is a block diagram of components of a system 200 that generates the 3D image of regions 202 of an object 204 based on fluorescent illumination (e.g., administered by a fluorescent illumination administration device 206) imaged using a sequence of time spaced images captured by at least three imaging sensors 207A-C, in accordance with some embodiments of the present invention. System 200 may implement the acts of the method described with reference to FIG. 1, optionally by a processing unit 208 of a computing unit 210 executing code instructions 212A stored in a program store 212.

The systems and/or methods (e.g., implemented by code instructions executed by processor(s)) improve on the 2D TOVI method (invented by the same authors of the present application), by generating 3D images that are superior over the 2D images. The 3D images provide improved deeper depth data (e.g., the location of blood vessels and/or other regions within the 3D image), reduce noise from scattering of the fluorescent illumination (by the tissues), correct diffusion (of the fluorescent illumination agent from the vessels), correct blurring from residual motion artifacts, and/or compensate for distortion. The 3D images provide improved spatial and/or temporal resolution over the 2D images. Additional details of the TOVI method are found with reference to the following publications, the contents of which are incorporated herein by reference in their entirety:

V. Kalchenko, K. Ziv, Y. Addadi, N. Madar-Balakirski, I. Meglinski, and M. Neeman, "Combined application of dynamic light scattering imaging and fluorescence intravital microscopy in vascular biology," Laser Phys. Lett., 7(8), 603-606, 2010.

V. Kalchenko, N. Madar-Balakirski, I. Meglinski, and A. Harmelin, "In vivo characterization of tumor and tumor vascular network using multi-modal imaging approach," J. Biophotonics, 4(9), 645-649, 2011.

V. Kalchenko, D. Israeli, Y. Kuznetsov, and A. Harmelin, "Transcranial optical vascular imaging (TOVI) of cortical hemodynamics in mouse brain," Sci. Rep. 4, 5839, 2014.

V. Kalchenko, Y. Kuznetsov, I. Meglinski, and A. Harmelin, "Label free in vivo laser speckle imaging of blood and lymph vessels," J. Biomed. Opt., 17(5), 050502, 2012.

V. Kalchenko, D. Israeli, Y. Kuznetsov, I. Meglinski, and A. Harmelin, "A simple approach for non-invasive transcranial optical vascular imaging (nTOVI)," J. Biophotonics, 8(11-12), 897-901, 2015).

The systems and/or methods described herein generate 3D images that include previously hidden vascular structures located deeper inside the object (e.g., tissue, brain), provide a functional imaging approach that may be used to characterize blood perfusion functions in real-time, and/or may be used to generate a real-time 3D imaging system.

As used herein, the term global shape means a depth map (e.g., implemented as a matrix, and/or image) denoting the depth of regions (and/or other structures) of the object in the perpendicular direction of the surface of the object (i.e., at a certain vantage point). It is noted that the generated 3D image may be an improvement of the global shape, for example, in terms of resolution and/or quality.

It is noted that a simple 2D depth map of the cranium without fine intracranial structures may define the 3D global shape. In the 2D case, the depth map (also termed Z-depth) may be implemented as a gray level image or a matrix that contains information related to the distance of the surfaces of scene regions from a viewpoint. Such depth map may be computed using a 2 imaging sensor stereo setup. However, the result is a coarse estimation that contains many distortions and places of missing information. The 3-Y setup described herein provides additional viewpoints that are used in order to render a high quality depth map, which is used to generate the 3D image.

The 3-Y setup provides additional computational improvements over a standard 2D stereo imaging system. The 3-Y setup may be arranged to provide triangulation abilities, which may be used to compute a unique solution for a global shape of the object. Three (or more) independent distortion datasets (e.g., matrixes) may be computed. The distortion dataset may be used to improve the quality of the generated 3D image, for example, fed into a neural network that generates the 3D image. The 3-Y setup may generate data used to complete missing lateral parts based on combination of data from the different points of view.

For clarity and simplicity, the implementation using three imaging sensors 207A-C is described herein. However, it is noted that one skilled in the art may select to implement more than three imaging sensors 207A-C, for example, to further improve the resolution of the regions within the generated 3D image. Imaging sensors 207A-C are designed to rapidly acquire a sequence of images (each separated by an interval of time) in real time, for example, about 5-10 images per second, or about 11-20 images per second, or about 1-4 images per second, or other rates. Exemplary hardware implementations of imaging sensors include complementary metal oxide semiconductors (CMOS) based light sensors.

Optionally, system 200 includes a laser(s) and another imaging sensor(s) 207D. Laser and sensor 207D are designed to perform laser speckle imaging (LSI). The LSI data may be used with the generated 3D image to create real-time 3D images of regions 202 within object 204. Laser and sensor 207D may be positioned at the center of imaging sensors 207A-C. The location of laser and sensor 207D is designed to reduce or eliminate geometrical distortion.

Optionally, object 204 includes a portion of a living mammal, for example, a human, a pig, a mouse, a dog, and a sheep. Object 204 may include, for example, a portion of the head of the living mammal, a portion of a tumor, and/or a portion of the heart.

Optionally, regions 202 of object 204 include one or more of: blood vessels, arteries, veins, lymphatic vessels, cerebrospinal fluid (CSF) containing lumens (e.g., chambers, vessels), an air filled lumen associated with the digestive system (e.g., intestine), and a urine filled lumen associated with the urinary system (e.g., ureter).

Optionally, fluorescent illumination administrative device 206 injects fluorescent illumination agent(s) (e.g., contrast) into region(s) 202 of object 204. Fluorescent illumination administrative device 206 may be implemented, for example, as a manual syringe, an automated syringe programmed to inject a defined amount of fluorescent illumination agent at a defied amount of time, an intravenous (IV) drip, orally administered agent (i.e., drinking the agent), or other implementations.

Computing unit 210 may be implemented as, for example, a client terminal, a server, a computing cloud, a mobile device, a desktop computer, a thin client, a Smartphone, a Tablet computer, a laptop computer, a wearable computer, glasses computer, and a watch computer. Computing unit 210 may include locally stored software that performed one or more of the acts described with reference to FIG. 1, and/or may act as one or more servers (e.g., network server, web server, a computing cloud) that provides services (e.g., one or more of the acts described with reference to FIG. 1) to one or more client terminals 214 over a network 216, for example, providing software as a service (SaaS) to the client terminal(s) 214, providing an application for local download to the client terminal(s) 214, and/or providing functions using a remote access session to the client terminals 214, such as through a web browser.

Computing unit 210 receives imaging data captured by imaging sensors 207A-C using one or more imaging interface(s) 218, for example, a wire connection, a wireless connection, other physical interface implementations, and/or virtual interfaces (e.g., software interface, application programming interface (API), software development kit (SDK)).

Program store 212 stores code instructions implementable by processing unit 204, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, program store 212 may store code instructions 212A that execute one or more acts of the method described with reference to FIG. 1.

Computing unit 210 may include a data repository 220 for storing data, for example, a trained time similarity index classifier used to generate the 3D image (as described herein), and an adaptive filter used to stabilize the image of the regions of the object and/or correct light scattering (as described herein). Data repository 220 may be implemented as, for example, a memory, a local hard-drive, a removable storage unit, an optical disk, a storage device, and/or as a remote server 222 and/or computing cloud (e.g., accessed over network 216 using a data interface 224). It is noted that code instructions 212A may be stored in data repository 220, for example, with executing portions loaded into program store 212 for execution by processing unit 208.

Computing unit 210 may include data interface 224, optionally a network interface, for connecting to network 216, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing unit 210 may access one or more remote servers 222 using network 216, for example, to download updates of code instructions 212A.

Computing unit 210 may connect using network 216 (or another communication channel, such as through a direct link (e.g., cable, wireless) and/or indirect link (e.g., via an intermediary computing unit such as a server, and/or via a storage device) with one or more of:

Client terminal(s) 214, for example, when computing unit 210 acts as a server providing SaaS.

Server 222, for example, when server 222 is part of a remote monitor server, which may present the generated 3D images for remote viewing, for example, by specialists providing medical support during an operation on a patient.

A storage unit hosted by server 222 that stores one or more of the generated 3D images, and/or the data used to construct the 3D image, for example, the sequences of images captured by imaging sensors 207A-C. Storage unit hosted by server 222 may be implemented as, for example, a storage server, a computing cloud storage server, or other implementations.

Computing unit 210 includes or is in communication with a user interface 226 allowing a user to enter data and/or view presented data and/or view the generated 3D image. Exemplary user interfaces 226 include, for example, one or more of, a touchscreen, a display, a keyboard, a mouse, and voice activated software using speakers and microphone.

One or more acts of the method described with reference to FIG. 1 may be implemented by code instructions 212A stored in program store 212 (and/or stored in data repository 220) executed by processing unit(s) 208 of computing unit 210.

At 102, a sequence of images of fluorescent illumination of regions 202 of object 204 is received from each imaging sensor 207A-C. Each sequence includes multiple images, each image separated by an interval of time from the previous and next image in the sequence. The sequences may be captured simultaneously and/or in parallel.

Optionally, each image is associated with a time of acquisition, for example, a tag indicative an absolute time (i.e., relative to a global clock) and/or a relative time (e.g. elapsed time from the previous image). An exemplary method of determining relative time is described, for example, by G. Molodij, E. N. Ribak, M. Glanc, and G. Chenegros, "Enhancing retinal images by extracting structural information," Opt. Comm. 313, 321-328 (2014)), incorporated herein by reference in its entirety.

For example, imaging sensors 207A-C are positioned to image the blood vessels of the brain of a mouse, positioned to image blood vessels of a tumor, image blood vessels of a human undergoing neurosurgery, or other application scenarios.

The 3-Y setup is based on a multiple stereo imaging approach. Three independent parallaxes data sets are generated, which inventors discovered is the minimum for calculating effective distortion matrixes (as described herein), and for computing the position of regions (and/or other structures) in the 3D imaging space. By applying the temporal indexation (described herein, also referred to herein as time similarity index), an accurate global shape of object 204 may be obtained. The fine detailed information of regions 202 (e.g., blood vessels 3D architecture of the brain) is determined (e.g., using a statistical classifier, and/or neural network) that processes the parameters described herein together.

At 103, LSI data is received from laser and/or sensor 207D. The received images are created based on reflections of the laser speckle projection captured by sensor 207D. The LSI may be used to generate the 3D image in real-time (in block 108), using the LSI as an independent reference. The LSI may be used, for example, when imaging through the intact skull, to correct distortions due to scattering.

The LSI data may include reflective multiple parallax image data that may be obtained as an alternative reference of the global shape independently from the fluorescence illumination.

The LSI may be used to determine a 3D flow map of blood vessels. The flow map may be correlated with the created volume-dataset of the location of the blood vessels. The LSI may be used to correct 3D coordinates of the regions of the volume-dataset. For example, the analysis (e.g., described with reference to block 104) that determines that certain image elements are part of a blood vessel (i.e. region) may be corrected using the LSI data. For example, image elements that are identified as blood vessels and for which the LSI data shows flowing blood may be confirmed as blood vessels. For example, image elements initially identified as blood vessel, however are not associated with flowing blood based on the LSI data may be corrected to indicate that such image elements are not blood vessels.

Referring now back to FIG. 1, at 104, the sequence(s) are analyzed to create a volume-dataset indicative of the depth of each respective region of the object, optionally by designing depth values for the image elements (e.g., pixel, voxel) of the regions. The volume-dataset may be represented as a depth map, or depth matrix (relative to a certain view point), or coordinates in the imaging space, or other implementations.

Exemplary analysis methods are described with reference to blocks 106A-F. The methods described with reference to blocks 106A-B may be performed in parallel, and/or sequentially, and/or in combination to generate the volume-dataset indicative of the depth (i.e., location) of each image element. Optionally, the methods described with reference to blocks 106C-F may be performed in parallel, and/or sequentially, and/or in combination with the methods described with reference to blocks 106A-B, to improve the volume-dataset, for example, improve the accuracy and/or resolution of the volume-dataset.

The volume-dataset may be generated based on a local correlation tracking technique (LCT), which is an image alignment method between two zones of interest.

The analysis of the sequence of images may be performed using a trained time similarity index classifier. As used herein, the term time similarity index classifier means a machine learning method, for example, a neural network, a statistical classifier a decision tree, a set-of-rules, regression methods, support vector machine, k-nearest neighbor, and the like. The trained time similarity index classifier may receive as input a computed initial location of each respective image element (e.g., based on the computed parallax-datasets described with reference to block 106A), and pattern(s) of changes in fluorescent imaging at each respective image element (e.g., based on the computed time similarity index described with reference to block 106B), and outputs the volume-dataset based on a computed maximum correlation of the location of each respective region and/or image elements of each region. The maximum correlation may be computed using a maximum probability estimation that may be implemented as a stochastic estimator depending on the localization, the time indexation, and/or the symmetry of a system. The 3D image may be generated based on the volume-dataset.

Optionally, a spatio-temporal distortion compensation matrix (STDCM) is computed to correct the depth (i.e., Z coordinate) of each image element (e.g., point, pixel, voxel) of each region (e.g., blood vessel). The STDCM is a matrix (or other implementation of representation) of the depth of regions (e.g., points, voxels) perpendicular to a certain viewing direction relative to the object. The STDCM includes weighted coefficients that may be applied to an initial volume-dataset of depth coordinates, to correct the depth coordinates. The STDCM may be used to correct the x-y-z coordinates of a 3D global shape (e.g., cranium), allowing rendering of the 3D (x-y-z) position of each region (e.g., blood vessel) within the 3D global shape (e.g., cranium). The STDCM is computed based on the methods described with reference to blocks 106A and/or 106B, and may be computed based on the methods described with reference to blocks 106C-E. The STDCM takes into account multiple spatial and/or temporal parameters, as described herein.

Optionally, at 105, an adaptive filter is applied to each sequence. The adaptive filter may be applied as part of the analysis of the sequences, applied prior to and/or during the analysis described with reference to blocks 104 and/or 106A-F.

The adaptive filter is designed to stabilize the imaged regions of the object, and/or correct light scattering. The adaptive filter is designed to improve spatial resolution of the location of each image element. The adaptive filter is designed to reduce noise during variations in intensity of the fluorescent illumination.

When trans-skin imaging is performed (i.e., the object is a living mammal, and the fluorescent illuminated regions are blood vessels and/or other fluid filled lumens in the body), the adaptive filter is designed to remove and/or reduce scattering of light coming from diffusive layers including the skin.

The adaptive filter is designed to improve the spatial resolution and/or reduce noise during fluorescence intensity variations of the sequence of images. The adaptive filter is applied despite the fast change of the visible imaged regions with time. The adaptive filter may be implemented based on an astronomical computational technique termed Kappa-Omega Adaptive filter that is based on 3D Fourier transforms. The adaptive filter significantly improves quality of unsupervised image registration of motion degraded images acquired during dynamic optical imaging of brain vasculature.

A deep field scattering removal (in the super-Gaussian assumption) may be applied. Multiple scattering results in image blurring may be modeled as a result of convolution with an unknown kernel. The point-spread function of the scattering medium may be obtained, for example, using a Monte-Carlo simulation, performed according to an optical model of biological tissues.

The fluorescence emission may be assumed to act as a Lambertian surface in photometric reconstructions. A super-Gaussian background subtraction may be applied to improve the image quality. It appears that the attenuation of a wave propagating in a certain direction is attributable to scattering in other directions (by conservation of energy), for example, as described with reference to Tatarskii, V. I.," *The effects of the turbulent atmosphere on wave propagation*", *Jerusalem: Israel Program for Scientific Translations*, 1971. The stochastic approach of scattering to describe the photon propagation such as laser beam propagation through atmospheric turbulence or the light through an interstellar medium is based on a probability density function to define screen models able to fit the scattering effect, for example, as described with reference to Hill, R. J., Frehlich, R. G.," *Probability distribution of irradiance for the onset of strong scintillation*", *JOSAA*, 14, 17, 1530-1540 (1997), Andrews, L. C., Phillips, R., L., Sasiela, R. J., Parenti, R., *"PDF Models for Uplink to Space in the Presence of Beam Wander"*, *Proc. of SPIE Vol.* 6551, 655109, (2007), and Johnson, M. D.; Gwinn, C. R.," *Ultra-high-resolution Intensity Statistics of a Scintillating Source* ", *Ap. J.*, 755, 2, (2012). However, in contrast, in trans-skin imaging of living mammals, fluorescence emission yields photometric enhancement in air that are superior to reflectance images. The fluorescence emission may behave as a Lambertian surface due to its isotropic emission. The point-spread function of the scattering medium may be obtained in a Monte-Carlo simulation, performed according to the optical model of biological tissues. The fluorescence reflectance acts as a Lambertian surface in photometric reconstructions, for example, as described with reference to A. M. Bronstein, M. M. Bronstein, M. Zibulevsky, Y. Y. Zeevi, *"Quasi-maximum likelihood blind deconvolution of images acquired through scattering media"*, *Biomedical Imaging: Nano to Macro, IEEE* 10.1109/*ISBL*2004.1398547 (2004), I. Sato, T. Okabe, and E Sato, *"Bispectral photometric stereo based on fluorescence"* in *Proc. IEEE CVPR*, 3, 6 (2012), T. Treibitz, Z. Murez, B. G. Mitchell, and D. Kriegman, *"Shape from fluorescence"*, in *Proc. ECCV*, 3, 6 (2012), and Z. Murez, T. Treibitz, R. Ramamoorthi, D. Kriegman, *"Photometric Stereo in a Scattering Medium"*, *IEEE International Conference on Computer Vision*, 10.1109/*ICCV.*2015.390. (28) D. Nandy, J. Ben-Arie, *"Shape from recognition: a novel approach for 3-D face shape recovery"*, *IEEE Trans. Image Process.*, 10, 206-217 (2001). For emission, a super-Gaussian sparse function provides a good approximation for image restoration through scattering media. For example, as described with reference to Bronstein et al.

Optionally, the adaptive filter is implemented as the super-Gaussian background subtraction to remove the scattering effect of the media (e.g., skin). The super-Gaussian background subtraction may provide an adequate stochastic approach. In terms of mathematic representation:

$$I_{filt}(i,j) = \frac{e^{\frac{-(i^2+j^2)}{2\sigma^2}}}{\sum_i \sum_j I_{raw}(i,j)}$$

Where:

$I_{fil}(i,j)$ denotes the adaptive filter (i.e., spatial filter function), $I_{raw}(i,j)$ denotes a certain current raw image of the sequence of received images having pixel dimensions denoted as i by j, and σ denotes the Gaussian parameter.

Inventors discovered that an optimal correction of the image is obtained when the image information entropy is minimum, for example, as described with reference to G. Molochj, E. N. Ribak, M. Glanc, G. Chenegros, *"Enhancing retinal images by nonlinear registration"*, Opt. Comm. 342, 157-166, 2015. In terms of mathematical representation, the optimal correction is denoted as:

$$I_{cor}(i,j)=I_{raw}(i,j)I_{fil}(i,j)$$

Examples of images produced with the adaptive filter in comparison to images produced without the adaptive filter are described below with reference to FIGS. 17-18.

Figure 3:
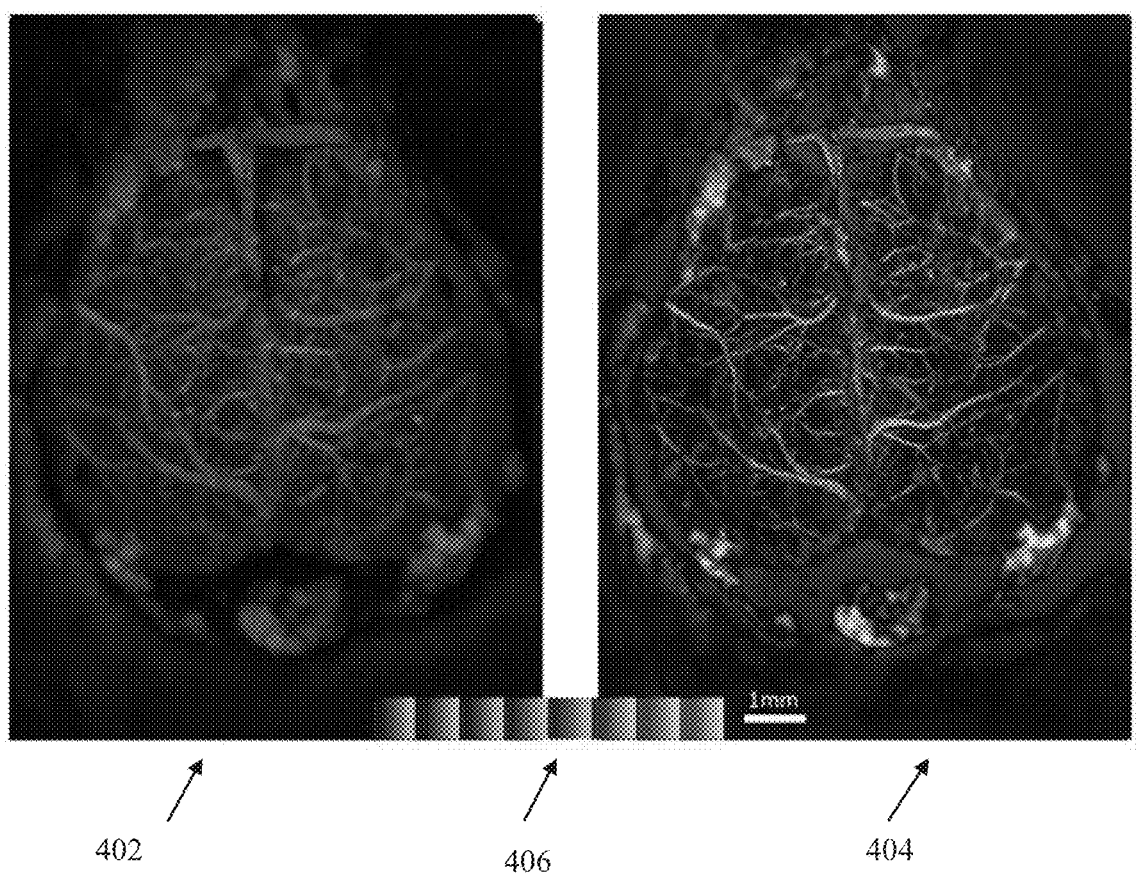
FIG. 3 depicts a comparison of a sequence of eight hundred (800) stacked images before and after application of the adaptive filter, in accordance with some embodiments of the present invention.

Reference is now made to FIG. 3, which depicts a comparison of a sequence of eight hundred (800) stacked images before 402 and after 404 application of the adaptive filter (the Kappa-Omega Adaptive filter) on the same sequence, in accordance with some embodiments of the present invention. Sequence 404 is visibly sharper (i.e., less noise) and/or with higher resolution in comparison to the raw image sequence 402. A temporal color coding (color bar 406) is applied to sequences 402 and 404 to estimate image quality.

Referring now back to FIG. 1, at 106A, the sequence(s) are processed to compute a respective parallax-dataset for each pair of imaging sensors. For example, in the exemplary 3-Y setup with three imaging sensors, a respective parallax-dataset is computed based on cameras 1-2, 2-3, and 1-3. Each parallax-dataset denotes volume data indicative of the 3D location of each image element of the regions. Each parallax-dataset may be computed independently.

Optionally, the parallax-datasets are processed to create the volume-dataset indicative of the location of each region within the image space. The processing may be performed, for example, using a machine learning method, optionally a neural network, optionally a convolutional neural network. The convolutional neural network exploits the local correlation to determine the depth in images that have been acquired from at least three different directions, optionally using an optical flow technique. It is noted that the described convolutional neural network based on three parallax-datasets provides improved computational efficiency in terms of improved results (e.g., resolution, accuracy) over methods that generate two images using two cameras, for example, as described with reference to J. Zbontar, Y. LeCun, "Computing the stereo matching cost with a convolutional7 neural network", Proceedings of the IEEE Conference on Computer Vision and Pattern Recognition, 2015, incorporated herein by reference in its entirety. Additional exemplary methods may be found, for example, in G. Molodij, E. N. Ribak, M. Glanc, G. Chenegros, "Enhancing retinal images by nonlinear registration", Opt. Comm. 342, 157-166, 2015, incorporated herein by reference in its entirety.

At 106B, the analysis is based on computing a time shape index parameter(s) (also referred to herein as time similarity index, also referred to herein as pattern(s)), which may include one or more parameters and/or patterns indicative of a change of the intensity of the fluorescent illumination over time at image elements. The time shape index is a temporal parameter related to the behavior (e.g., pattern) of fluorescent illumination intensity variation over time, for example, a function. The pattern may be computed based on the captured image sequences, which may include at least one image without any administered fluorescent illumination agent, and multiple images depicting the flow pattern of the administered fluorescent illumination agent. The sequences may include termination images, in which the fluorescent illumination agent has been removed from the regions of the object (e.g., removed from the blood circulation, and/or sufficiently diffused to a negligible concentration).

The term time shape index sometimes refers to the estimation of the similarity between two (or between groups of) image elements (e.g., pixels, voxels). The term time shape index parameter sometimes denotes the time evolution behavior of the image element. The term pattern sometimes denotes the result of spatial structures having similar (according to the requirement) estimated temporal behavior, i.e., similar shape index parameter(s) estimated based on the time similarity index.

The time similarity index may be used to classify (e.g., index) regions (e.g., internal microstructures) into one or more types according to time-dynamic interactions with the administered fluorescent agents.

Optionally, the STDCM is computed based on the computed time shape index parameters associated with the pattern(s) of fluorescent intensity over time at each respective region.

The sequences of fluorescent illumination may be analyzed (optionally on a local basis, e.g., per image element, and/or per group of neighboring image elements)) to determine patterns of time to maximum intensity of the fluorescent illumination, and/or time of approximately stable intensity of the fluorescent illumination.

The sequences of fluorescent illumination may be analyzed (optionally on a global basis), to determine the patterns relative to image elements and/or groups of neighboring image elements, for example, which groups of image elements experience the rise to maximum fluorescent illumination first, which groups experience the rise to maximum fluorescent illumination last, which groups experience the longest stable intensity of fluorescent illumination, and which groups experience the shortest intensity of fluorescent illumination.

Optionally, the analysis is performed per region and/or per group, based on linking image elements having similar patterns indicative of the change of intensity of the fluorescent illumination.

The analysis based on the patterns is performed to determine the type of the region. Exemplary types include: a bifurcation of a blood vessel, a first blood vessel at a higher tissue level crossing over a second blood vessel at a lower tissue level, an artery, a vein, a lymphatic vessel, cerebrospinal fluid (CSF) containing lumen, an air filled lumen associated with the digestive system, and a urine filled lumen associated with the urinary system.

Exemplary analysis methods based on the patterns and/or groups of imaging elements to determine the type include:

Differentiation of vessel bifurcation from vessel crossing over by the pattern of fluorescent illumination at the bifurcation or cross over image elements. Bifurcations are assumed to occur approximately simultaneously (i.e., blood in the vessel divides at the bifurcation at the same time) while crossing over of different vessels are assumed to occur at different times (i.e., as each vessel fills with the fluorescent agent depending on the location of the vessel).

Differentiation of arteries from veins according to the time of maximum fluorescent illumination, for example, arteries are assumed to fill with fluorescent agent first, followed by veins.

Identification of the type using a structural index similarity classifier trained using 3D imaging data associated (e.g., tagged) with defined types. The structural index similarity classifier may classify the image elements and/or regions according to what structure to expect at the 3D location based on structures located at the same 3D location (and/or relative to one another) in the training imaging data. For example, when a certain vessel appears in 70% of the training images at a certain location, and/or the certain vessel has an anatomical configuration that appears in 70%, the image elements may be classified as the certain vessel.

The computed time shape index parameters may be used to resolve structure and/or function (i.e., phenomena) according to spatial location. Optionally, the identified structure(s) and/or function(s) are correlated to the volume-data, for example, by color coding (or other labeling method) the region at certain locations according to the structure and/or function at the certain location. Alternatively or additionally, the structure(s) and/or function(s) are identified in view of the expected structure and/or function at the certain location, for example, when a vessel is expected next to another identified vessel, the presence of the vessel may be validated by the time shape index. Exemplary structure(s) and/or functions(s) include one or more of: fine structural details, type of blood vessel (i.e., artery or vein), topology indicating a bifurcation of a vessel or crossing over of vessels, blood vessel classification issues, fluorescent contrast extravasation, and normal functional state or abnormal behavior identification.

Optionally, the computed time similarity index is used to localize the scattering precursor before the propagation of the fluorescent light through tissues.

Inventors discovered that the classification of image elements (and/or regions and/or groups) into types may be performed using at least two parameters computed at respective image elements, including the time to maximum fluorescent intensity, and similarity of fluorescent intensity over time (i.e., maintenance over multiple images) and/or similarity of fluorescent intensity patterns of nearby image elements (according to the similarity requirement). Identification of a relatively slow rise time to maximum fluorescent intensity is sensitive for classification of the type. Due to the superimposition of the different fluorescent illumination patterns at different image elements, as the blood flows through the vessel, the slow rise time may be analyzed as corresponding to the blood flow (i.e., the fluorescent agents within the blood) through the vessel. The similarity of fluorescent intensity patterns over nearby image elements that are continuous with one another may indicate the presence of a continuous blood vessel. The similarity of fluorescent intensity patterns over time may indicate stagnation of blood, for example, an aneurysm or clot blocking blood flow in the vessel.

Image elements and/or groups identified as having a similar (or of the same) type and/or having similar patterns (according to a similarity requirement, e.g., a correlation value threshold or range indicative of the correlation similarity between the patterns, and/or a time similarity index between patterns) may be assigned similar colors. The similarity requirement may be selected, for example, to account for a margin of error in signal acquisition, and/or to group together clinically significant patterns.

Optionally, the patterns of fluorescent illumination (optionally per image element and/or per group) are represented as temporal functions. Optionally, the similarity between the patterns is computed based on similarity between the temporal functions. Optionally a temporal similarities index indicative of the similarity between the temporal functions is computed. The temporal similarities index takes into account the logarithmic sensitivity perceivable by humans (e.g., Weber-Fechner logarithmic law) and/or structural information provided by a statistical distance between the two functions (e.g., Manhattan distance).

In terms of mathematic representation:

Ic(t) denotes a current temporal function;

Ir(t) denotes a reference temporal function;

Alternatively or additionally, the described temporal similarities index (also referred to herein as structural similarities index) takes into account the sensitivity of the common sense described by a power law (e.g., as described with reference to K. Brecher, *"Should Astronomy Abolish Magnitudes?"*, American Astronomical Society, 199th AAS Meeting, id.40.02; *Bulletin of the American Astronomical Society*, 33, 1363, 2001) and the structural information obtained from the two functions (e.g., obtained by the Manhattan distance derived from the two functions). In terms of mathematical representation the following relationship may represent an improved efficiency of the computed temporal similarity:

$$S_i = \left[\frac{\text{Max}[I_r^2(t)]}{\delta_d}\right]^{1/3}$$

Si denotes the temporal assessment that defines the relative distance between Ic(t) (i.e., the current temporal function) by comparison with the reference temporal function denoted Ir(t). When Si is computed, the value of $\delta_d$ may be alternatively computed according to the following relationship:

$$\delta_d = \sum_{t=0}^{T} \frac{|I_c(t) - I_r(t)|}{I_c(t) + I_r(t)}$$

Si is related to the maximum value of the reference function Ir. In the term $\delta_d$, the measurement is related to the contrast. The structure relationship between the two functions comes from the comparison between the reference and the current image for example, by the Manhattan distance denoted as |Ic(t)-Ir(t)|.

As discussed herein, the time similarity index is used to classify (e.g., to index) internal structures into one or more types according to time-dynamic interactions with the administered fluorescent agents. More frequent and/or usual patterns may be detected (e.g., major arteries, such as in the brain) and/or otherwise hidden abnormalities may be detected (e.g., slow leakage of blood out of brain vessels due to a hemorrhagic stroke, and/or abnormal blood vessel angiogenesis in a tumor). The pattern is indicative for example, of the time to reach maximum intensity of the fluorescent illumination and/or the stability of the intensity of the fluorescent illumination. Image elements having similar patterns (e.g., according to the similarity requirement, for example, structural distance) are grouped together, for example, by a metadata tag and/or color denoting each group. The grouped image elements may be identified as one or more predefined types indicative of structure or function, and are used to resolve structural detail, for example, to differentiate between arteries and veins.

Additional exemplary methods for computing similarity between temporal functions may be found, for example, in G. Molodij, E. N. Ribak, M. Glanc, G. Chenegros, "Enhancing retinal images by nonlinear registration", Opt. Comm. 342, 157-166, 2015, incorporated herein by reference in its entirety.

Figure 4:
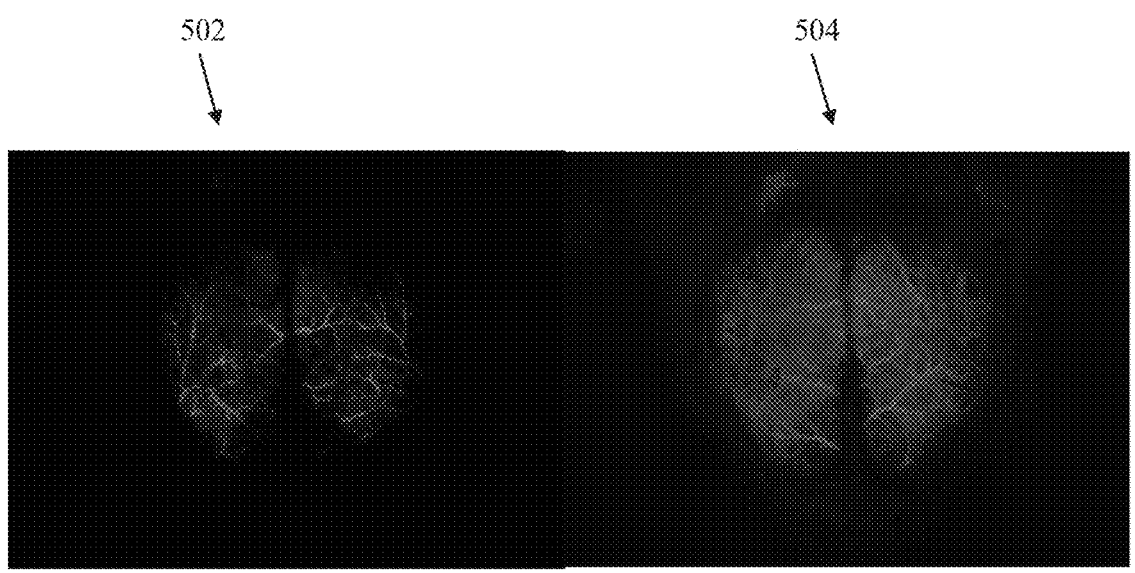
FIG. 4 includes a first image and a second image that are color coded according to image elements having similar patterns, in accordance with some embodiments of the present invention.

Reference is now made to FIG. 4, which includes a first image 502 and a second image 504 that are color coded according to image elements having similar patterns (according to the similarity requirement), in accordance with some embodiments of the present invention. The similarity of the patterns is computed based on the pattern of illumination at each image element over the image of the sequence. Optionally, the similar patterns are classified according to vessel type. Image 502 depicts arteries (in red) and image 504 depicts veins (in blue).

Figure 5:
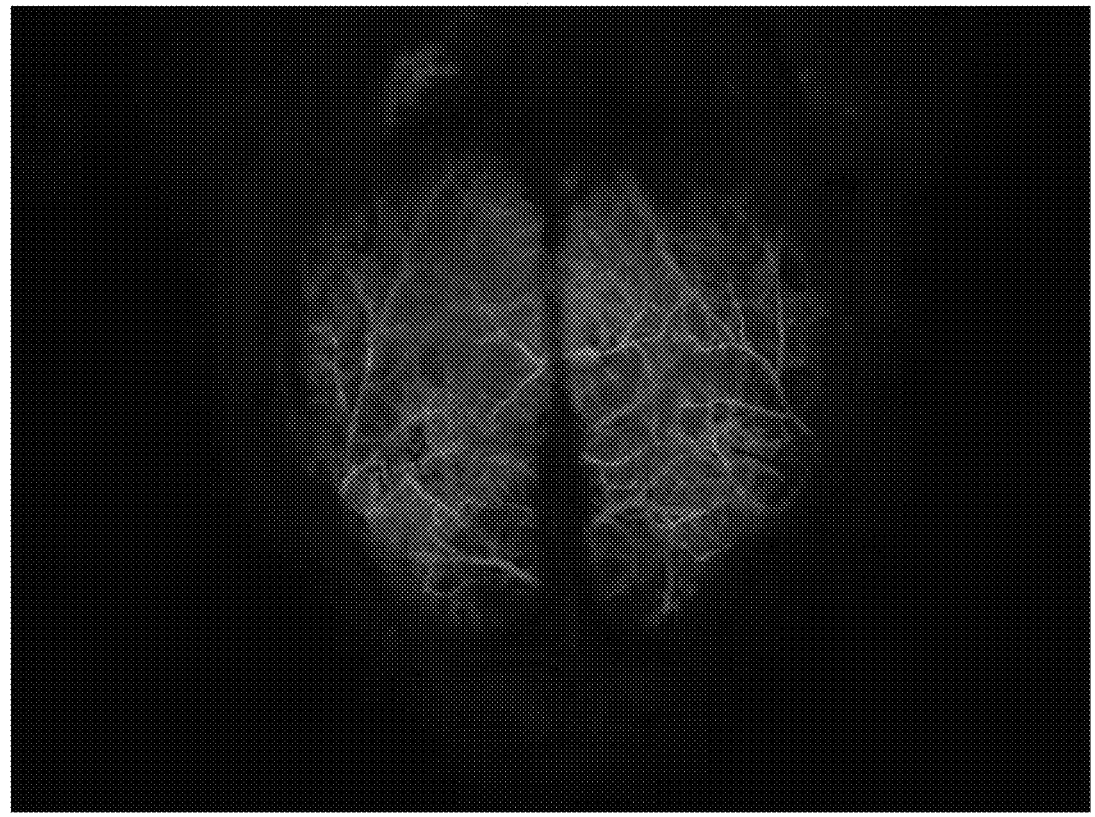
FIG. 5 is an image created by superimposing the images of FIG. 4, in accordance with some embodiments of the present invention.

Reference is now made to FIG. 5, which is an image created by superimposing images 502 and 504 of FIG. 4, in accordance with some embodiments of the present invention.

Referring now back to FIG. 1, optionally, at 106C, an isotropic reference is computed. The isotropic reference improves spatial resolution of the generated 3D image, when the 3D image is generated according to the isotropic reference.

The isotropic reference may be used to compute point spread function(s) (PSF), optionally by performing an adaptive unsupervised technique. An optimal point spread function may be used for spatial resolution improvement and/or image volume correction.

The isotropic reference may be used to automatically quantify the resolution of the 3D image using statistical methods, optionally based on the ergodic principle assumption. As used here, the ergodic principle is a stochastic principle that denotes that the mean estimate over time is equivalent to mean estimate over space.

The PSFs may be extracted from the superimposition of the accurate Laplacian and the cross correlation on the single raw image based on the ergodic principle assumption, for example, as described with reference to G. Molodij, S. Keil, T. Roudier, N. Meunier, S. Rondi, "Method for single image restoration based on the ergodic principle", J. Opt. Soc. Am. A. 27(11), 2459-2467, 2010, incorporated herein by reference in its entirety. PSFs may be determined and implemented as input into existing methods, for example, Blind algorithms, or Lucy-Richardson algorithm.

It is noted that the optimum kernel may be evaluated using an image quality assessment based on a stability estimator. Such stability assessment may be performed based on an adaptation of the Lyapunov exponent on a single image based on the ergodic principle. The determination of the stability estimator may be estimated from the spatial mean gradients values between the raw image and the generated image. The imaginary part value of the complex coefficient Sc denotes an estimate of the stability that is assigned a second order polynomial fit as large as possible. When a reference image exists, Sc is at the minimum. Sc is denoted as:

$$S_c = \text{Im}\left(\lim_{n\to\infty} \frac{1}{N} \sum_{i=1}^{N} \log_2\left(\frac{\nabla I_r(i)}{\nabla I_d(i)}\right)\right)$$

Alternatively or additionally, at 106D, a motion estimator is computed based on an analysis of changes in intensity of the fluorescent illumination of the regions. The motion estimator may be applied to the volume-dataset of depth locations to correct motion artifacts. It is noted that even small motion artifacts may spoil valuable information.

Optionally, the motion estimator is based on a K-Omega adaptive motion estimation approach that verifies the position of each image element (e.g., point, pixel, voxel) over time (i.e., over multiple images in the sequence).

Optionally, the motion estimator is used for image quality assessment, based on the estimation of the restoration stability using the raw image without any reference.

Alternatively or additionally, at 106E, a deconvolution parameter(s) is computed that compensates for scattering of the fluorescent illumination, and/or estimates diffusion of the fluorescent illumination agent leaking out of vessels. The deconvolution parameter(s) may be applied to the volume-dataset of depth data, to correct the volume-dataset. The corrected volume-dataset may include improved spatial resolution of the regions.

The deconvolution is an image restoration method that improves quality of the image (e.g., spatial resolution) based on the assumption that image burring may be mathematically represented by a convolution relation (e.g., function).

The deconvolution parameter may be computed based on the determined patterns of fluorescent intensity described with reference to block 106B.

It is noted that scattering may be especially problematic when imaging through an intact skull and through the intact skin.

The deconvolution may be computed based on an unsupervised image restoration method.

The deconvolution may be computed according to the computed PSF.

Alternatively or additionally, at 106F, structure tensors are computed based on the respective parallax shift of the imaging sensors. The volume-dataset is computed (and/or corrected) according to the computed structure tensors, for improving the depth and/or parallax sensitivity of the regions within the 3D image.

Structure tensors are computed to improve the depth and/or parallax sensitivity of the volume-dataset of depth data, for example, to improve the computation of depth and/or parallax of fluorescent illuminated blood vessels. Structure tensors may be computed for imaging elements (e.g., pixels, voxels, other imaging elements), or groups thereof.

Structure tensors may be computed for image sequences that were captured based on trans-skin imaging, where the imaging sensors are located externally to the skin of the target mammal being imaged for capturing images of the fluorescence that is emitted from tissues (e.g., blood vessels) below the surface of the skin.

Computation of the structure tensors for improvement of the depth and/or parallax of the volume-dataset improves computational efficiency of computational unit 210, by improving the clarity and/or accuracy of imaged structures (e.g., blood vessels which include fluorescence) lying below a diffusive medium (e.g., skin, tissue), for example, in comparison to the resolution obtained by other methods such as correlation based techniques which are limited by the size of the correlation window and/or which are applied to noisy data.

The local depth is inferred from the relative orientations of the imaging sensors (e.g., 207A-C) relative to object 204, optionally in combination with the temporal analysis (e.g., as described with reference to act 106, also referred to as the analysis based on the time similarity index) and/or in combination with the adaptive filtering (e.g., as described with reference to act 105).

At 108, the 3D image is generated according to the volume-dataset that stores the location of each region (e.g., by storing the location of each image element representing respective regions). Optionally, the 3D image is generated according to the multiple parallax-dataset, with corrections of the location of the regions performed as described herein.

Optionally, the 3D image is generated using a reconstruction process based on optical flow, optionally using a machine learning method, optionally, convolution neural network (CNN). The CNN may be designed to perform computations using a minimal amount of preprocessing, which improves computational efficiency of the computing unit.

Image elements identified as having a similar (or of the same) type and/or having similar patterns (according to a similarity requirement, e.g., a correlation value threshold or range indicative of the correlation similarity between the patterns) may be assigned similar colors.

Optionally, identified regions (e.g., type of region) of the volume-dataset are associated with visual marker(s) indicative of the computed type, for example, color image elements are color coded according to type, and/or intensity of image elements are designated according to type. The 3D image is generated based on the assigned visual marker(s). Alternatively or additionally, image elements having similar patterns (according to the similarity requirement) are assigned similar colors.

At 110, the generated 3D image is presented locally (e.g., on display 226), stored locally (e.g., in data repository 220), and/or transmitted to a remote location (e.g., client terminal(s) 214, server(s) 222) for remote presentation and/or remote storage.

At 112, blocks 102-110 are iterated, optionally in real-time, for example, during a medical procedure, such as neurosurgery, and/or as part of a monitoring process, for example, to monitor progression of stroke in a patient. The generated 3D image may be dynamically updated, as a sequence of images and/or as a movie.

Figure 6:
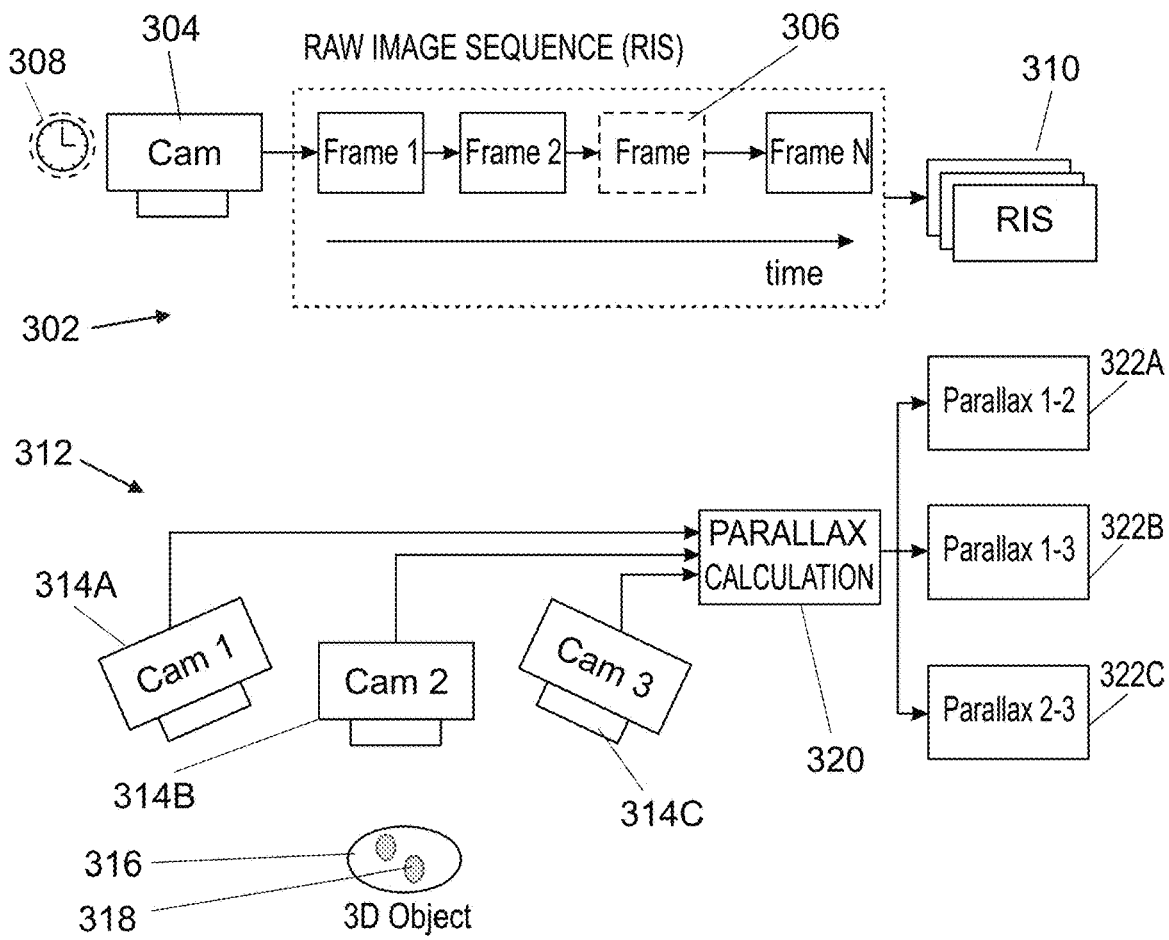
FIG. 6 is a block diagram depicting exemplary dataflow of a process for generating a 3D image of an object based on sequences of time spaced images of fluorescent illumination applied to the object, in accordance with some embodiments of the present invention.
Figure 6:
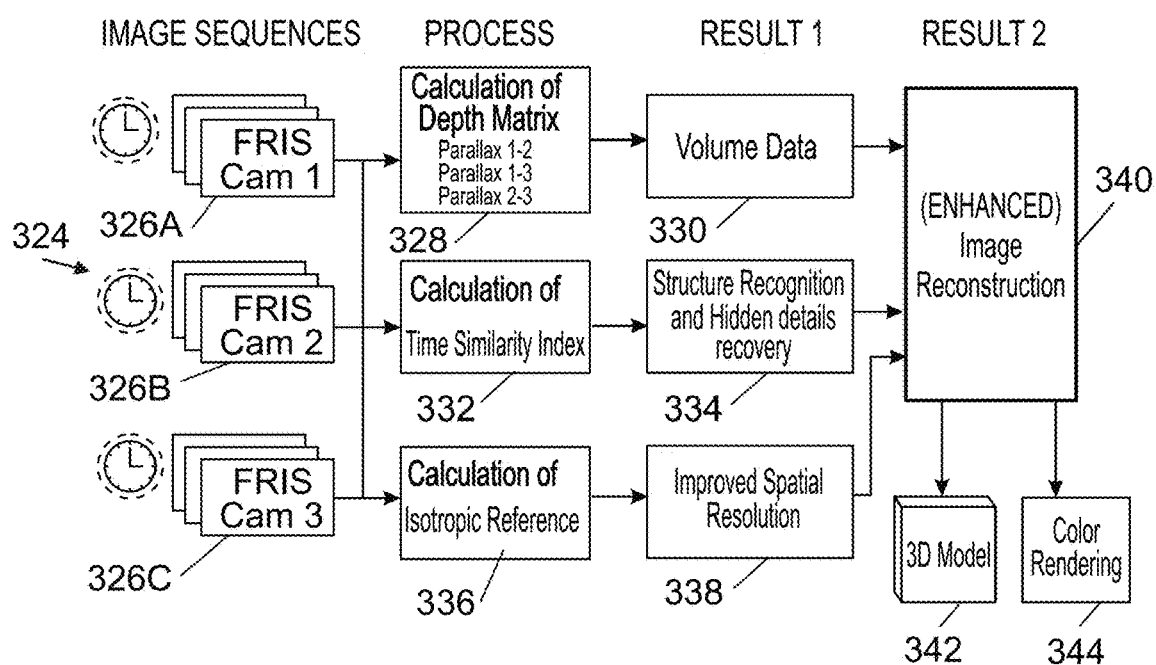

Reference is now made to FIG. 6, which is a block diagram depicting exemplary dataflow of a process for generating a 3D image of an object based on sequences of time spaced images of fluorescent illumination applied to the object, in accordance with some embodiments of the present invention. The dataflow described with reference to FIG. 6 may be based on and/or implanted in accordance with the method described with reference to FIG. 1, and/or system 200 described with reference to FIG. 2.

Dataflow 302 depicts the process of generating a raw image sequence. A camera 304 acquires multiple frames 306. Frames are separated from each other by a time interval. Frames are associated with a time 308, optionally stamped with the current time according to a clock. Frames are stored as a raw image sequence (RIS) 310.

Dataflow 312 depicts the computation of three parallax-datasets. Each of cameras (i.e., image sensors) 314A-B capture a RIS of object 316 that includes one or more regions 318 having administered fluorescent illumination agent(s). The RIS's are processed by parallax calculation code instructions 320 (e.g., implemented by processor(s) of a computing unit) to compute parallax-datasets 322A-C that include depth data of the locations of regions 318. Parallax-dataset 322A is based on cameras 314A and 314B. Parallax-dataset 322B is based on cameras 314A and 314C. Parallax-dataset 322C is based on cameras 314B and 314C. Parallax-datasets 322A-C may be implemented as STDCMs.

Dataflow 324 depicts the computation of the 3D image (i.e., 3D model) based on the acquired RIS. RIS 326A-C are acquired by the cameras as described by dataflow 302. RIS 326A-C are used (in parallel and/or sequentially and/or independently) to:

Calculate a depth matrix 328 which is used to provide a volume-dataset 330 of the location of regions of the object, as described with reference to dataflow 312. The volume data 330 may be reconstructed based on the computation of STDCMs.

Calculate a time sensitivity index 332, which is used to recognize structures and recover hidden details 334, as described herein.

Calculate an isotropic reference 336, which is used to improve spatial resolution 338 of the generated 3D image.

Volume data 330, structure recognition and hidden details 334, and improved spatial resolution 338 data are processed to perform image reconstruction 340 of the regions within the object. A 3D model 342 is generated, which may be associated with color rendering 344 indicative of the type of structure, as described herein.

Figure 7:
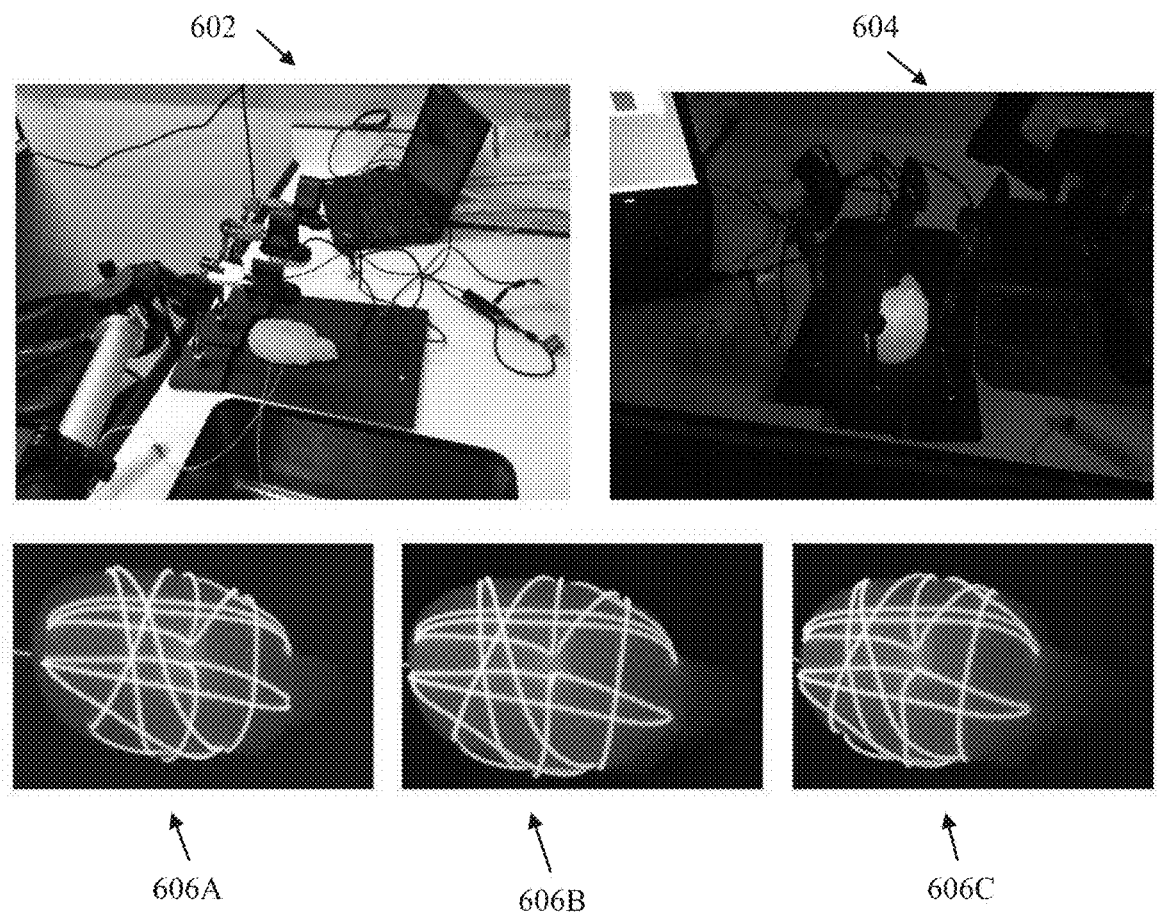
FIG. 7 includes photos an exemplary 3-Y setup of an imaging experiment performed by the inventors, in accordance with some embodiments of the present invention.

Reference is now made to FIG. 7, which includes photos 602 604 of an exemplary 3-Y setup of an imaging experiment performed by the inventors, in accordance with some embodiments of the present invention. A phantom shape was used to simulate a brain. Tubes were used to simulate blood vessels. A fluorescent illumination agent was injected into the tubes to simulate circulation of blood within the blood vessels. Images 606A-C represent raw images of the phantom and tubes filled with the administered fluorescent agent that are captured by a different imaging sensor of the 3-Y setup.

Figure 8:
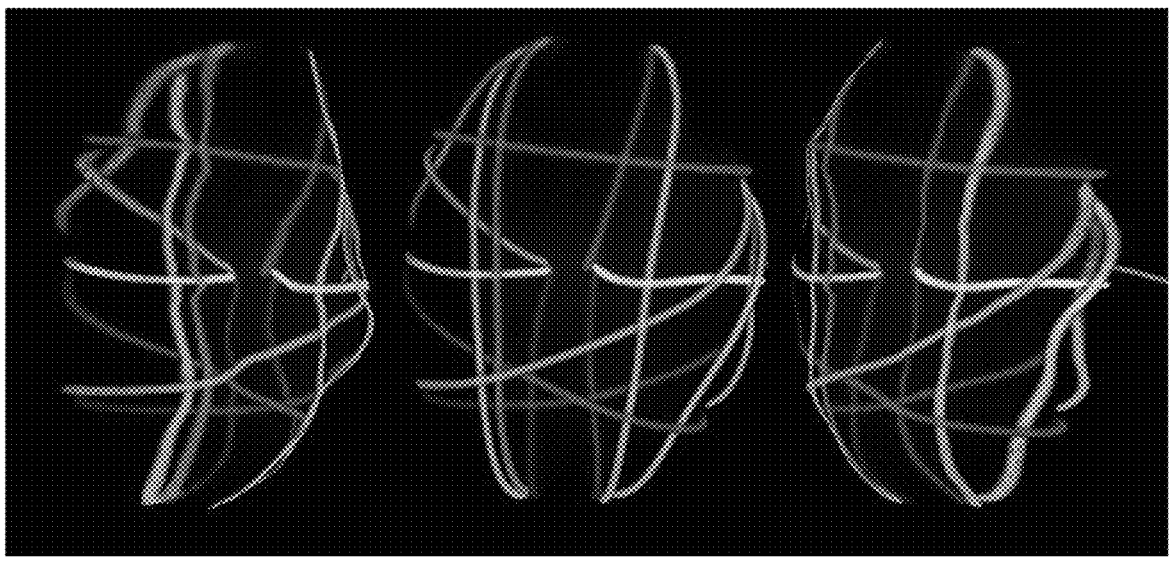
FIG. 8 is a 3D image generated using the 3-Y setup of FIG. 7 and computed using the systems and/or methods described herein, in accordance with some embodiments of the present invention.

Reference is now made to FIG. 8, which depicts the generated 3D image using the 3-Y setup of FIG. 7 and computed using the systems and/or methods described herein, in accordance with some embodiments of the present invention. The 3D image is shown rotated, at three different vantage points. In order to know the relative position between the tubes (above or below the tube crossing), the sensitivity of the depth reconstruction is artificially enhanced (using bumps of tubes at the crossing region). The precise shape of the tubes themselves may be derived as described herein, for example, from a second order treatment using the neural network process described herein.

Figure 9:
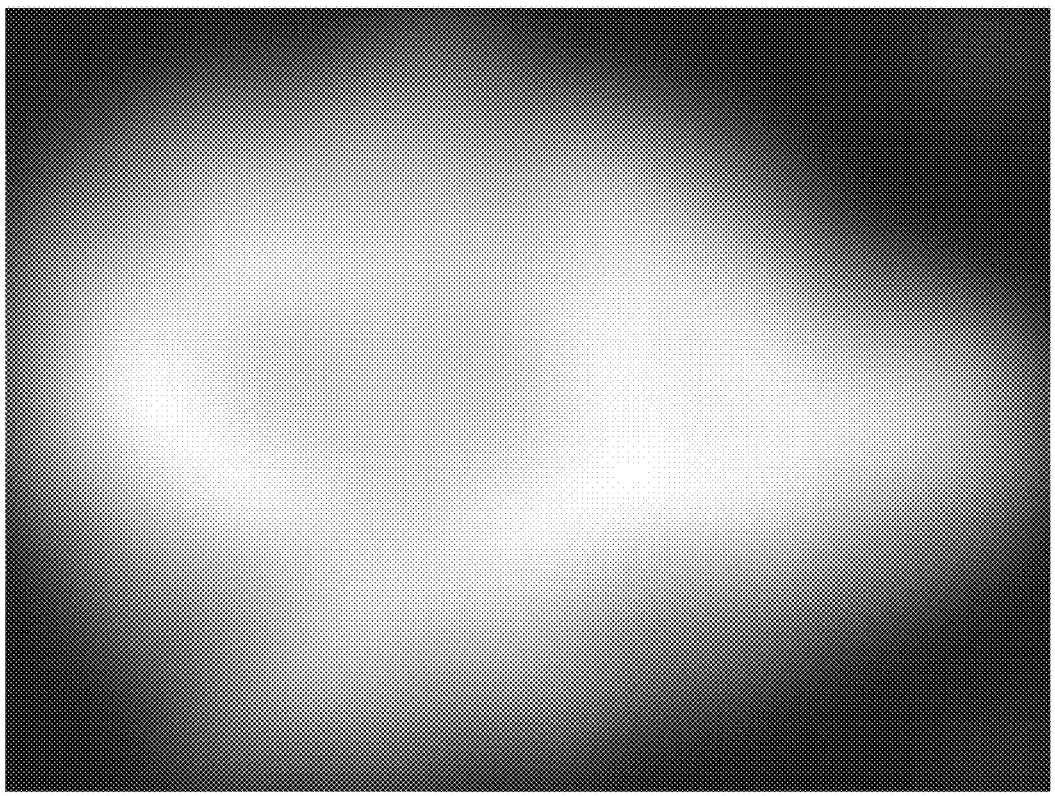
FIG. 9 is an image of the 3D global shape (i.e. the depth map, also termed the volume-dataset used to generate the 3D image) captured using the 3-Y setup, in accordance with some embodiments of the present invention.

Reference is now made to FIG. 9, which is an image of the 3D global shape (i.e. the depth map, also termed the volume-dataset used to generate the 3D image) captured using the 3-Y setup, in accordance with some embodiments of the present invention. The depth map is represented as a gray level image or matrix that includes data related to the distance of the surface of the tubes (of the setup shown in FIG. 7) perpendicular to a certain viewpoint. The image shown in FIG. 9 is computed without using the temporal indexation described herein, highlighting the contribution of the temporal indexation in generating a high resolution and high quality 3D image. A local correlation tracking technique from the 3-Y setup is used to determine the parallaxes. The level of gray is an indication of the depth. Note that the structures and the scattering of the fluorescent illumination are mixed, rendering a coarse shape, which further highlights methods described herein the correct for the scattering in generating the high quality 3D image.

Figure 10:
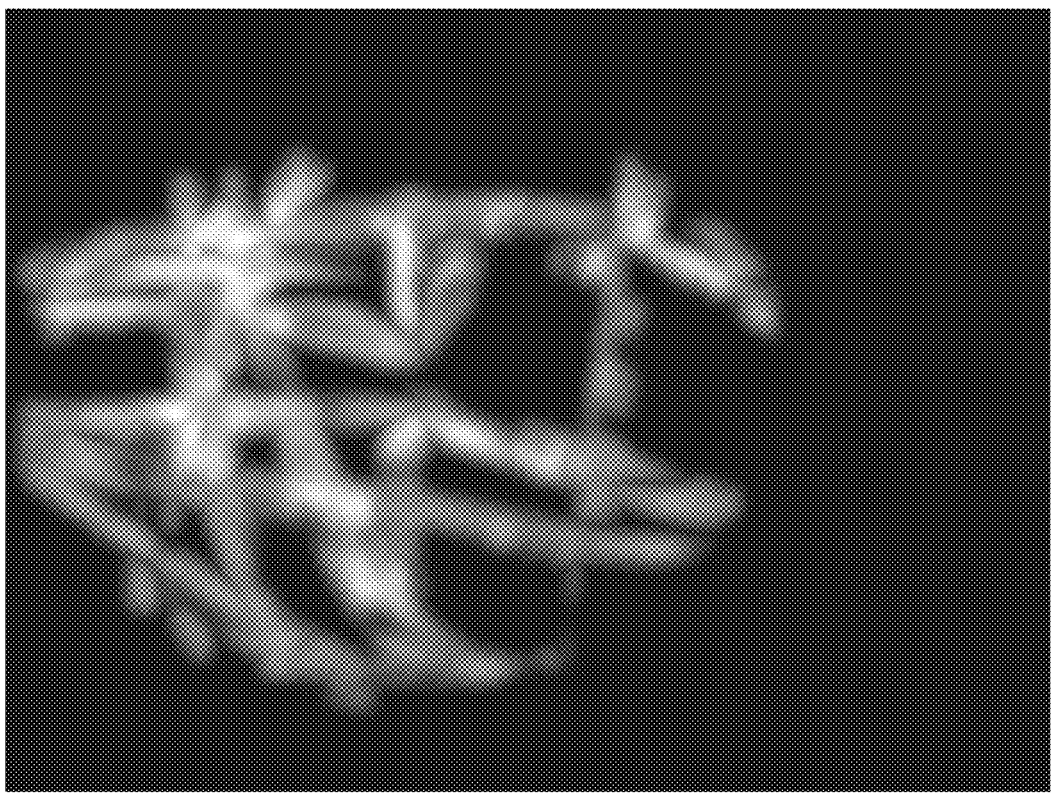
FIG. 10 is an image generated based on a computed STDCM, depicting a structured shape related to fine structural detail of the position of the positions of the tubes of the setup shown in FIG. 7, in accordance with some embodiments of the present invention.

Reference is now made to FIG. 10, which is an image generated based on a computed STDCM, depicting a structured shape related to fine structural detail of the position of the positions of the tubes of the setup shown in FIG. 7, in accordance with some embodiments of the present invention. Note the improvement of FIG. 10 in relation to FIG. 9. The image of FIG. 10 includes depth reconstruction using the temporal indexation described herein. The level of gray is an indication of the depth. The fine structures (tubes) are taken in consideration in the 3D shape reconstruction.

Figure 11:
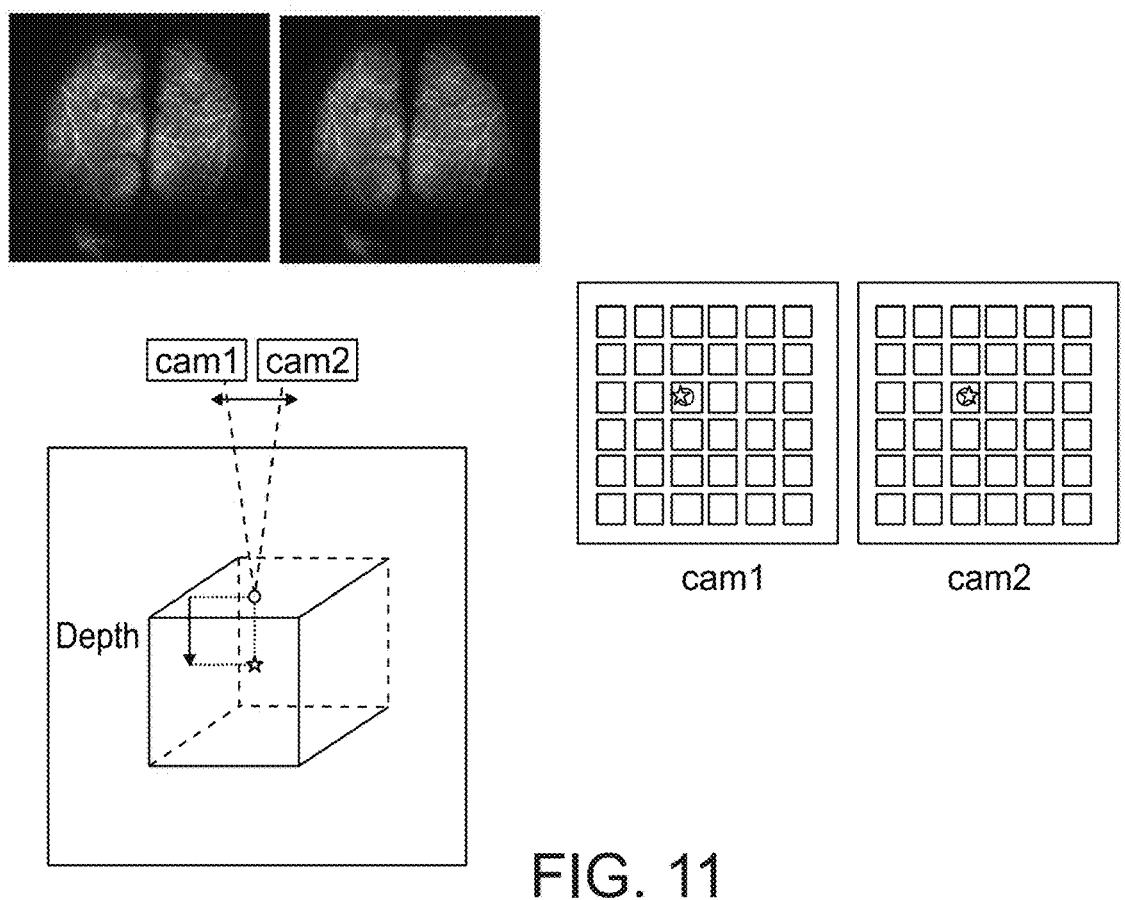
FIG. 11 is a schematic depicting a setup for computation of the parallax-dataset between two of three cameras of the 3-Y setup described herein, in accordance with some embodiments of the present invention.

Reference is now made to FIG. 11, is a schematic depicting a setup for computation of the parallax-dataset between two of three cameras of the 3-Y setup described herein, in accordance with some embodiments of the present invention.

Figure 12:
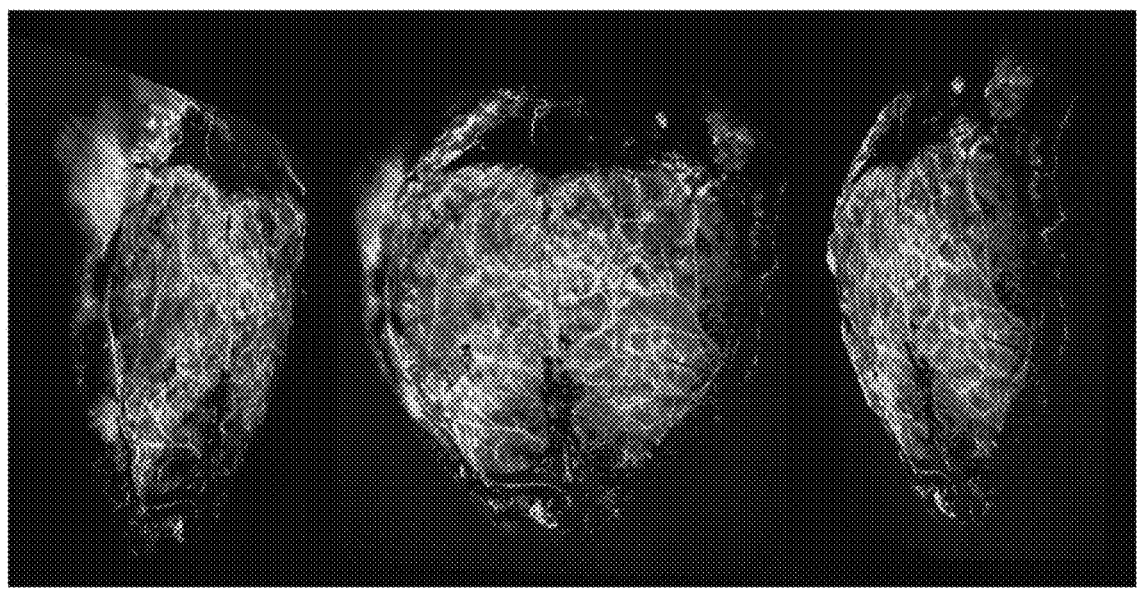
FIG. 12 is a 3D image generated using the setup shown in FIG. 11, in accordance with some embodiments of the present invention.

Reference is now made to FIG. 12, which includes a 3D image generated using the setup shown in FIG. 11, in accordance with some embodiments of the present invention. The STDCM is computed based on the temporal indexation method described herein, and used to generate the 3D image.

Figure 13:
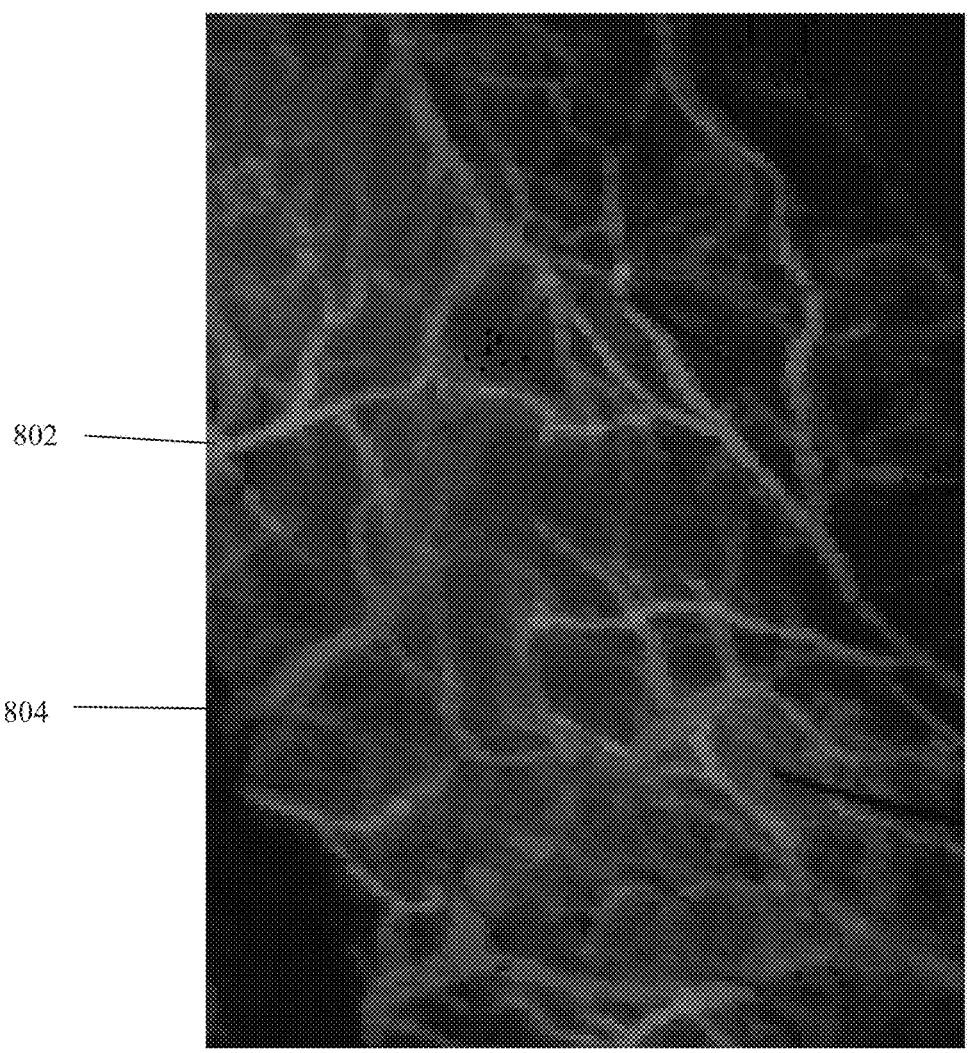
FIG. 13 is an image of indications on the 3D topology of two embedded vessel networks, generated based on the setup shown in FIG. 11, in accordance with some embodiments of the present invention.

Reference is now made to FIG. 13, which is an image of indications on the 3D topology of two embedded vessel networks, generated based on the setup shown in FIG. 11, in accordance with some embodiments of the present invention. The image of FIG. 13 shows fine details in the generated 3D image. Arteries 802 are shown in red. Veins 804 are shown in blue. The temporal indexation described herein (e.g. with reference to block 106B) is used to determine two matrix of distortion from the local correlation in order to extract the 3D topology of the two embedded networks (i.e., arteries and veins). It is noted that the precision of the reconstruction is limited by the 2 setup cameras (one parallax measurement) of FIG. 11.

Figure 14:
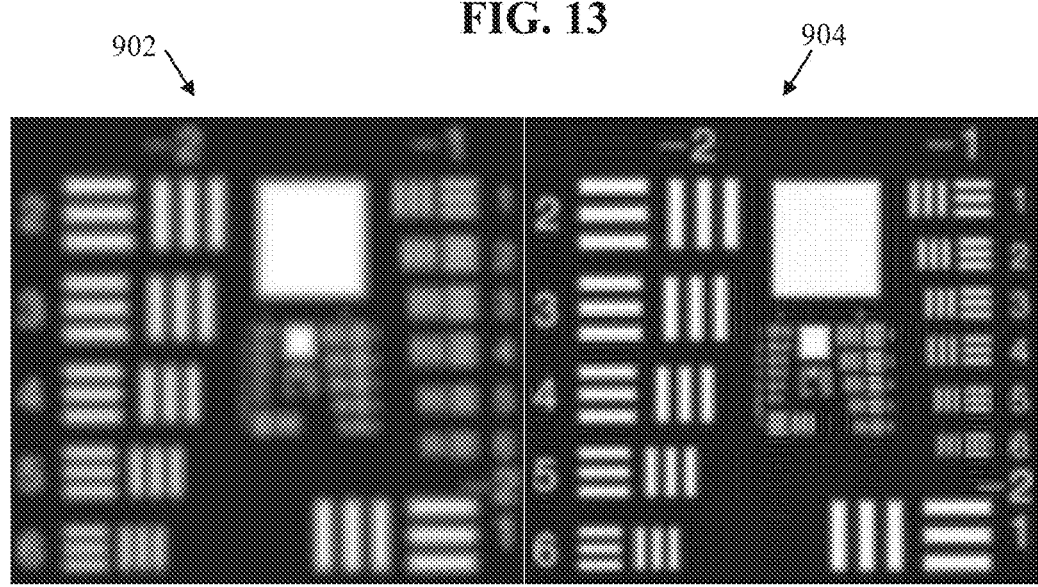
FIG. 14 includes images depicting an example of the automated image restoration method, in accordance with some embodiments of the present invention.

Reference is now made to FIG. 14, which includes images depicting an example of the automated image restoration method, in accordance with some embodiments of the present invention. Blurry image 902 is restored to image 904 using the isotropic reference automated method and stability estimation, without reference, as described herein, for example, with reference to block 106C.

Figure 15:
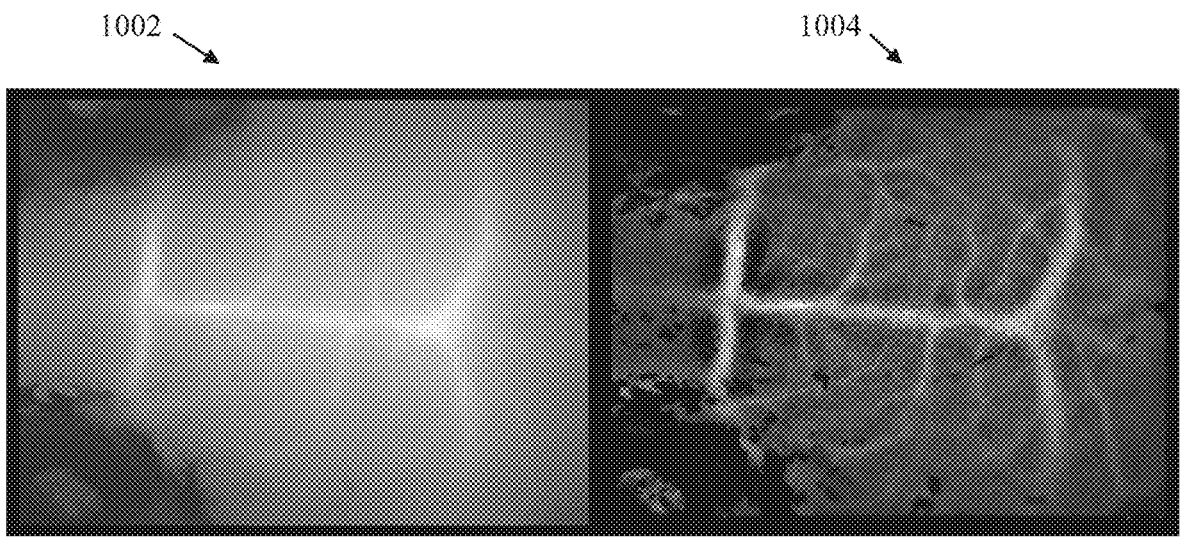
FIG. 15 includes images depicting an example of the automated image restoration method on real trans-skin imaging, in accordance with some embodiments of the present invention.

Reference is now made to FIG. 15, which includes images depicting an example of the automated image restoration method on real trans-skin imaging, in accordance with some embodiments of the present invention. Blurry image 1002 is restored to image 1004 using image restoration methods using the isotropic reference method, as described herein, for example, with reference to block 106C.

Figure 16:
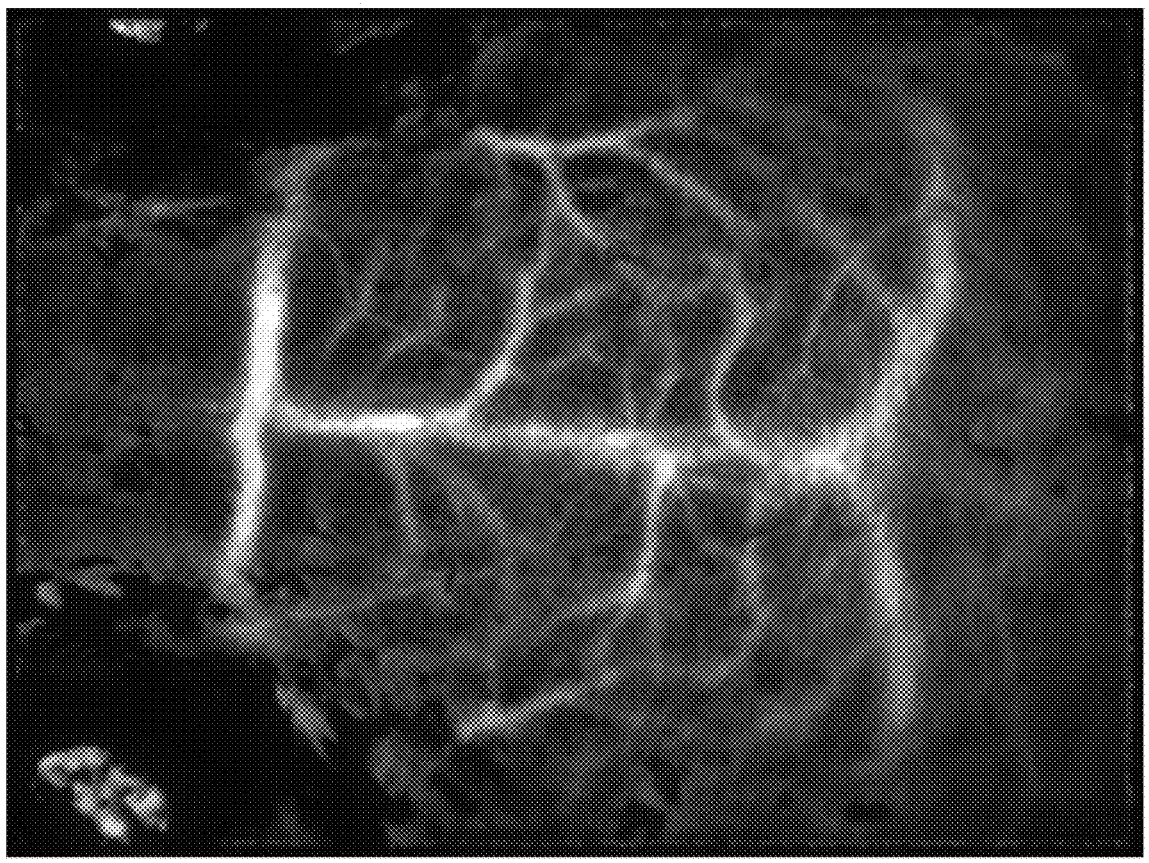
FIG. 16 is an image generated using the time similarity indexation method applied to the imaging data of FIG. 15, in accordance with some embodiments of the present invention.

Reference is now made to FIG. 16, which is an example of an image generated using the time similarity indexation method (e.g., as described with reference to block 106B) applied to the imaging data of FIG. 15, after the image restoration methods using the isotropic reference method (e.g., as described with reference to block 106C) and the K-omega registration method have been applied to the sequence, in accordance with some embodiments of the present invention.

Figure 17:
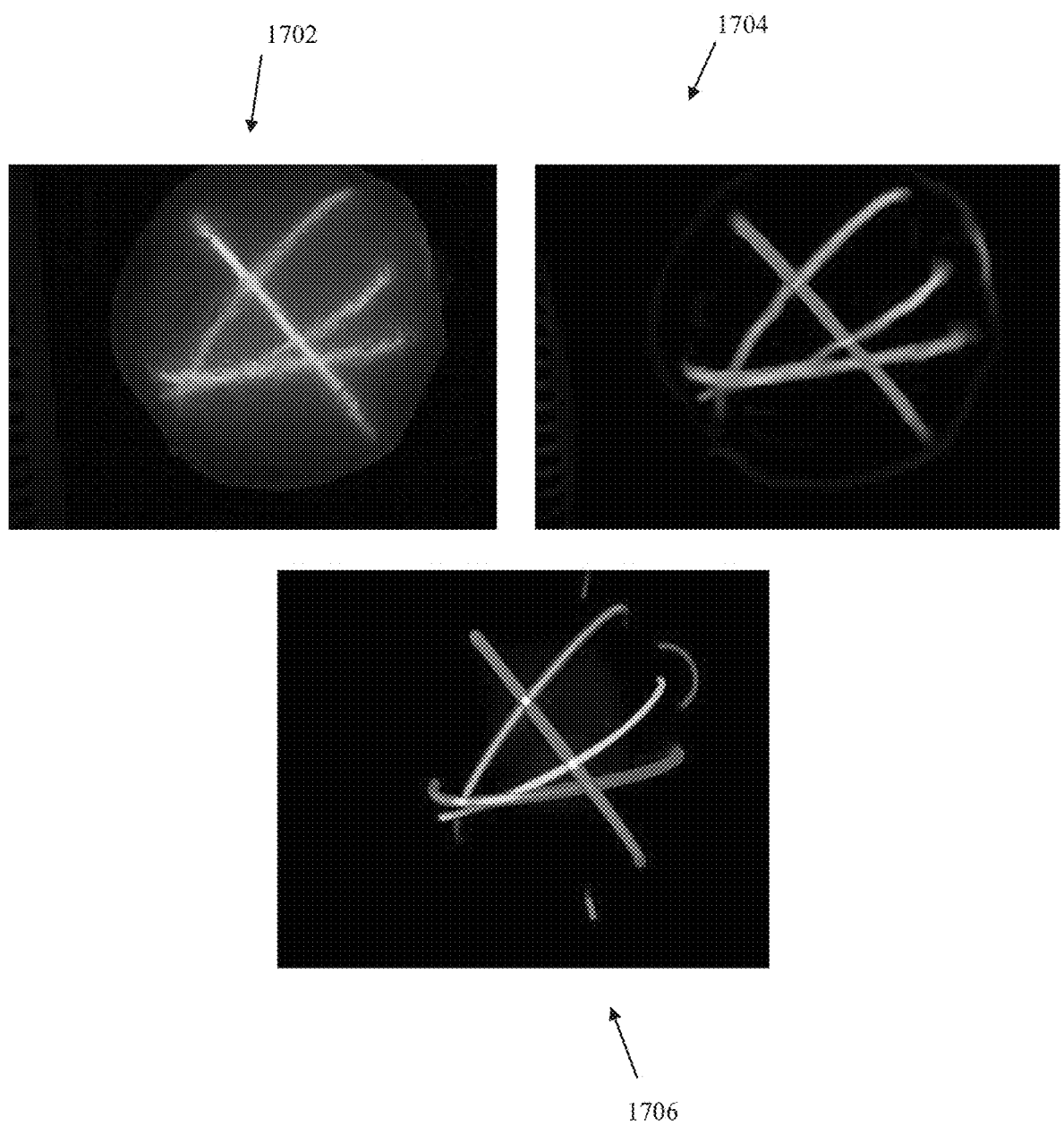
FIG. 17 which includes 3D images computed as part of a laboratory experiment using a phantom, to evaluate the effects of the adaptive filter on the quality of the sequence of captured images, in accordance with some embodiments of the present invention.
Figure 18:
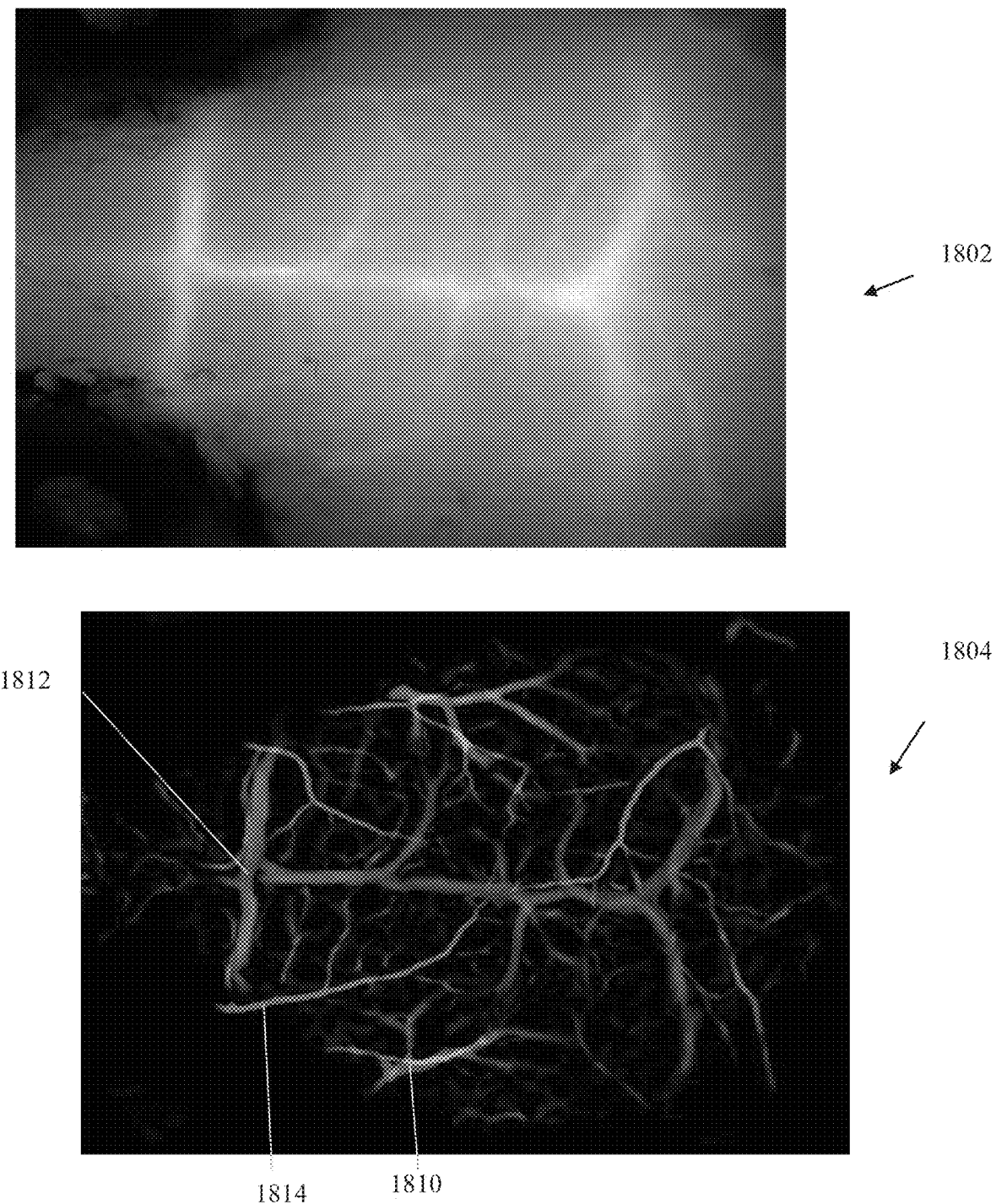
FIG. 18 includes 3D images computed from sequences of images captured as part of an experiment, to evaluate the effects of the adaptive filter on the quality of the generated 3D image, in accordance with some embodiments of the present invention.

Reference is now made to FIG. 17, which includes example 3D images 1702-1706 computed as part of a laboratory experiment using a phantom, to evaluate the effects of the adaptive filter on the quality of the 3D images, in accordance with some embodiments of the present invention. The evaluated adaptive filter was implemented as the super-Gaussian background subtraction denoted $I_{filt}(i,j)$, as described herein. Images 1702-1706 were created by capturing sequences of images of the phantom as fluorescence entered tubes within the phantom, using the system set-up as described herein (e.g., with reference to system 200 of FIG. 2, and/or FIG. 5) and processing of the image sequence as described herein (e.g., FIG. 1 and/or FIG. 6).

Image 1702 is created from the image sequences captured by the imaging sensors observing the phantom through a diffusive layer (e.g., simulating skin). It is noted that image 1702 is at a relatively lower resolution in comparison to image 1704 and image 1706. Moreover for image 1702, determining the order of enlightenment of the fluorescent filled tubes of the phantom from the sequence of images is more difficult in comparison to images 1704 and 1706.

Image 1704 is created by applying the adaptive Gaussian filter to the raw image sequence used to create image 1702. It is noted that the scattering effect is removed from image 1704 (in comparison to image 1702), and that the order of enlightenment of the tubes in image 1704 is clearly identified (in comparison to image 1702).

For relative comparison with images 1702 and 1074, image 1706 is created by capturing the sequence of images of the phantom as fluorescence entered tubes within the phantom, without the diffusive layer. Reference is now made to FIG. 18, which includes example 3D images 1802-4 computed from sequences of images captured as part of an experiment, to evaluate the effects of the adaptive filter on the quality of the 3D images, in accordance with some embodiments of the present invention. Images 1802-4 were computed from sequences of images captured from a real observation of brain vascularization through the skin. Images 1802-4 were created by capturing sequences of images of the cranium as fluorescence entered blood vessels within the brain, using the system set-up as described herein (e.g., with reference to system 200 of FIG. 2, and/or FIG. 5) and processing of the image sequence as described herein (e.g., FIG. 1 and/or FIG. 6).

Image 1802 was created without application of the adaptive filter, and by implementation of the temporal indexation method to the image sequences that included scattered light (which was not corrected for by the adaptive filter). Image 1804 was created by application of the adaptive filter, and implementation of the temporal indexation method to the image sequences which were corrected to remove the scattered light. The evaluated adaptive filter was implemented as the super-Gaussian background subtraction denoted $I_{filt}(i,j)$, as described herein. The structure indexation method described herein was implemented on the image sequences using color-coding to distinguish the nature of the blood vessels. Arteries 1810 are denoted by the color red. Veins 1812 are denoted by the color blue. Skin vessels 1814 are denoted by the color green.

Figure 19:
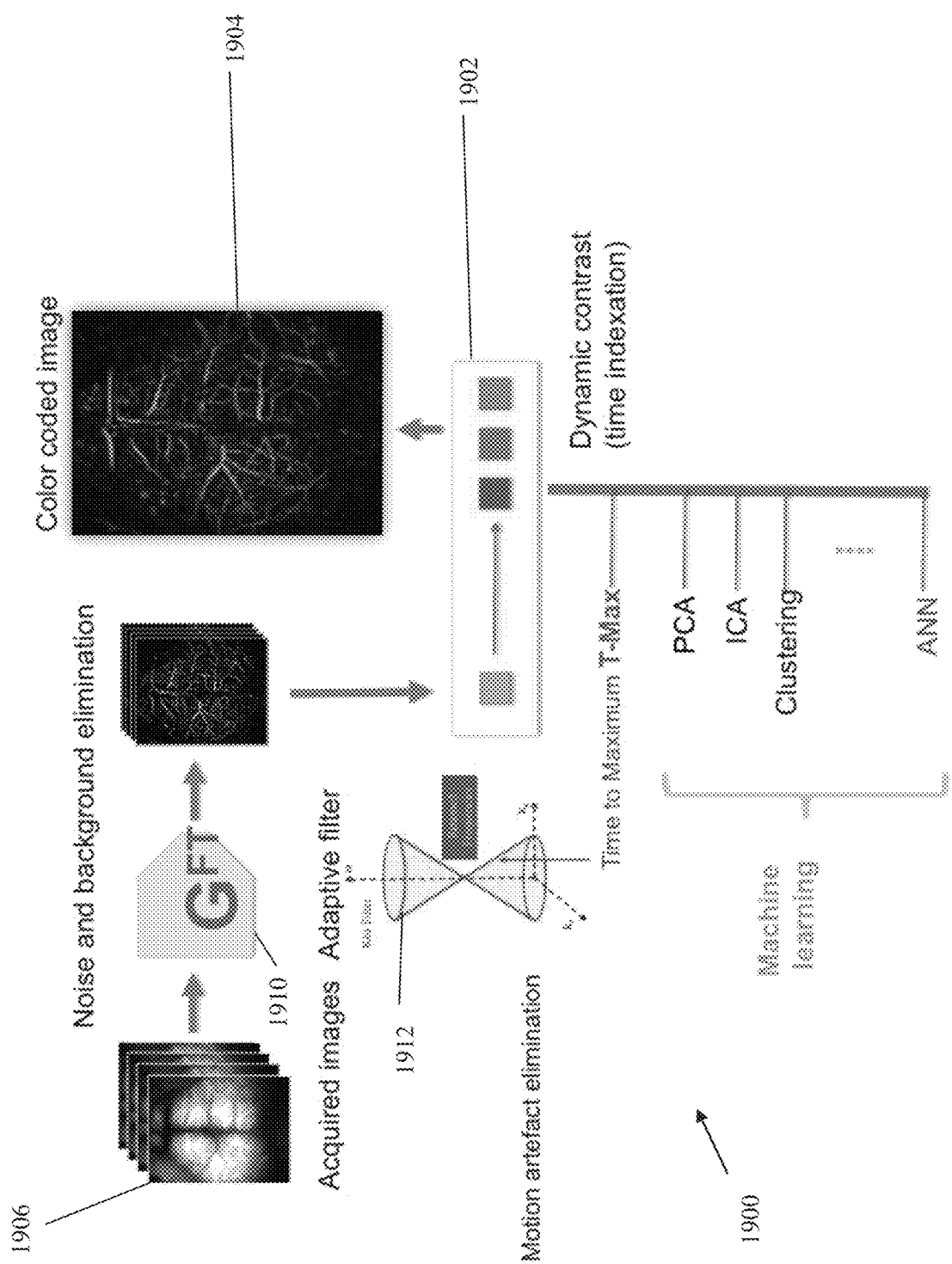
FIG. 19 is a schematic depicting an exemplary implementation of a neural network based architecture for computation of the 3D image, in accordance with some embodiments of the present invention.

Reference is now made to FIG. 19, which is a schematic depicting an exemplary implementation of a neural network based architecture 1900 for computation of the 3D image indicative of the depth of each respective fluorescent enhanced region of the object from sequences of captured images, in accordance with some embodiments of the present invention. Neural network 1902 performs the time indexation and/or computes the local depth, and/or reduces scattering, to compute a 3D image 1904 (that is optionally color coded according to type of structure, for example color coded to distinguish between arteries, veins, and skin vessels) from captured sequences of images 1906 of the object, as described herein. Captures images 1906 are processed for removal of scattering light by application of adaptive filter 1908 (e.g., the Gaussian filter described herein with reference to act 105 of FIG. 1), and elimination and/or reduction of motion artifacts 1910 (e.g., as described with reference to act 106D of FIG. 1).

Neural network 1902 may perform the computations described with reference to one or more of acts 106A-F described with reference to FIG. 1, and optionally generation of 3D image(s) described with reference to act 108 of FIG. 1.

Neural network 1902 may be stored, for example, in data repository 220 and/or program store 212 of computational unit 210, and/or as part of code 212A, for execution by processing unit(s) 208 of computational unit 210.

Neural network 1902 may analyze sequences of images of fluorescent illumination per group of neural mode images to determine patterns of time, instead of, for example, using standard segmentation methods that are difficult to implement due to the fast dynamic nature of the fluorescent intensity. Optionally, the neural network computes the temporal indexation based analysis (e.g., as described with reference to act 106B of FIG. 1) based on linking image elements having similar patterns indicative of the change of intensity of the fluorescent illumination.

Is it noted that implementation of neural network 1902 improves computational efficiency of the computing unit 210, for example, in terms of improved quality of the generated 3D image. Neural network 1902 appears to be sensitive to the local organization of the fluorescent illuminated structures of the object, which improves the analysis for detection of the bifurcation and/or cross ambiguity described herein.

Figure 20:
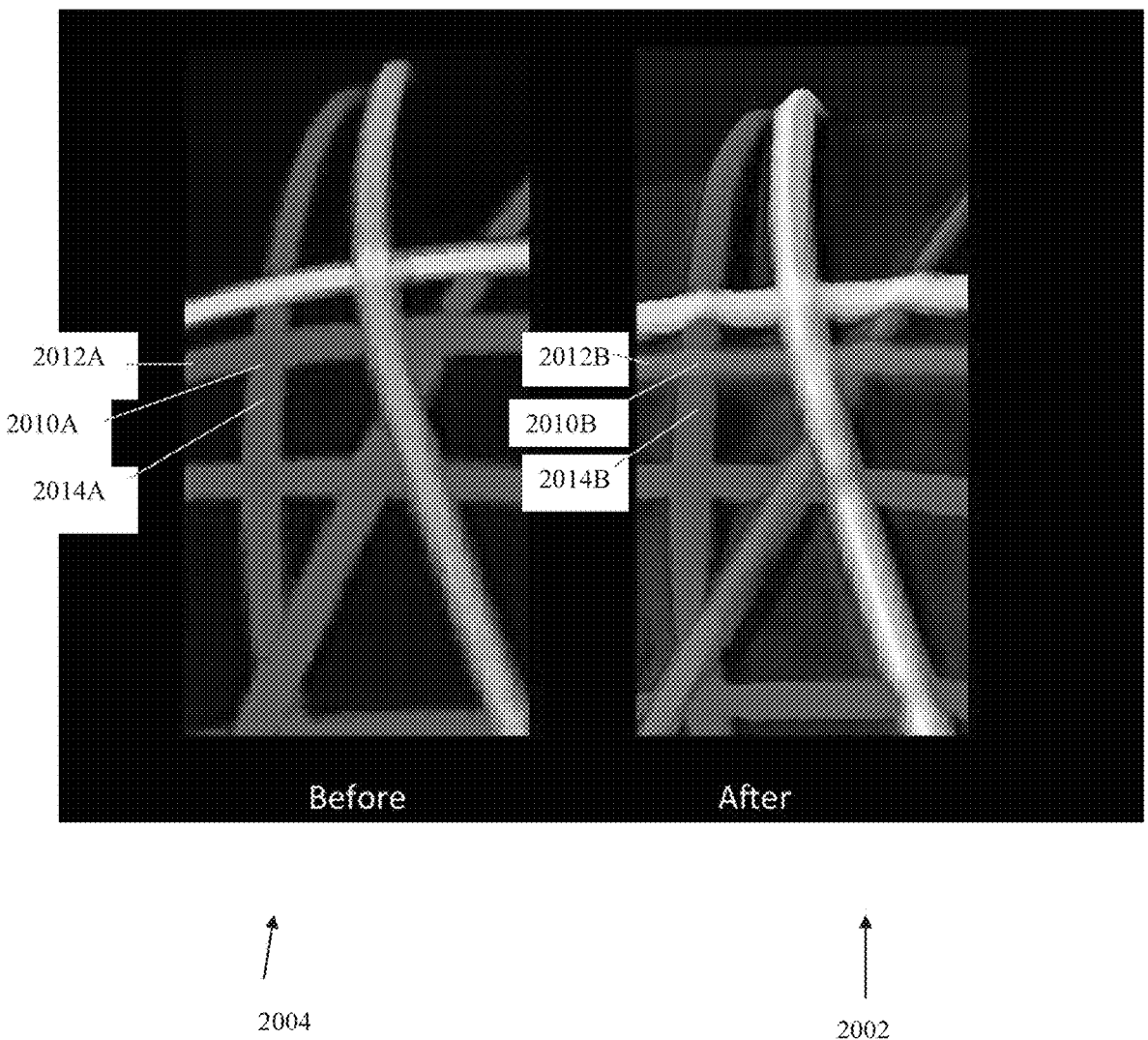
FIG. 20 includes a portion of a 3D image based on output of a neural network, depicting clarity of bifurcation and/or crossing of structures, in accordance with some embodiments of the present invention.

Reference is now made to FIG. 20, which includes a 3D image 2002 computed based on output of a neural network (e.g., as described herein and/or neural network 1902 of FIG. 19), depicting a resolution to the bifurcation and/or crossing ambiguity described herein, in accordance with some embodiments of the present invention. Image 2002 depicts clarity of bifurcation and/or crossing of structures (e.g., blood vessels). Image 2002 is compared to image 2004 which is computed using other methods, without the neural network. Images 2002-4 are based on sequences of images of the phantom experiment (described with reference to FIG. 17) captured as fluorescence entered tubes within the phantom, using the system set-up as described herein (e.g., with reference to system 200 of FIG. 2, and/or FIG. 5) and processing of the image sequence as described herein (e.g., FIG. 1 and/or FIG. 6 and/or FIG. 19). The local organization of the tubes in the 3D local space as shown in image 2002 (which is computed by the neural network) is determined more accurately in comparison to image 2004 (which is not computed by the neural network).

Ambiguities in bifurcation and/or crossing of tubes are resolved in image 2002, in comparison to ambiguities apparent in image 2004. For example, with reference to image 2004, at junction 2010A, it is unclear whether tube 2012A and tube 2014A are bifurcations, or which tube is higher and which tube is lower. The ambiguity is resolved in image 2002, where it is apparent that at corresponding junction 2010B, that corresponding tube 2012B crosses over tube 2014B (i.e., tube 2012B is located above tube 2014B).

Figure 21:
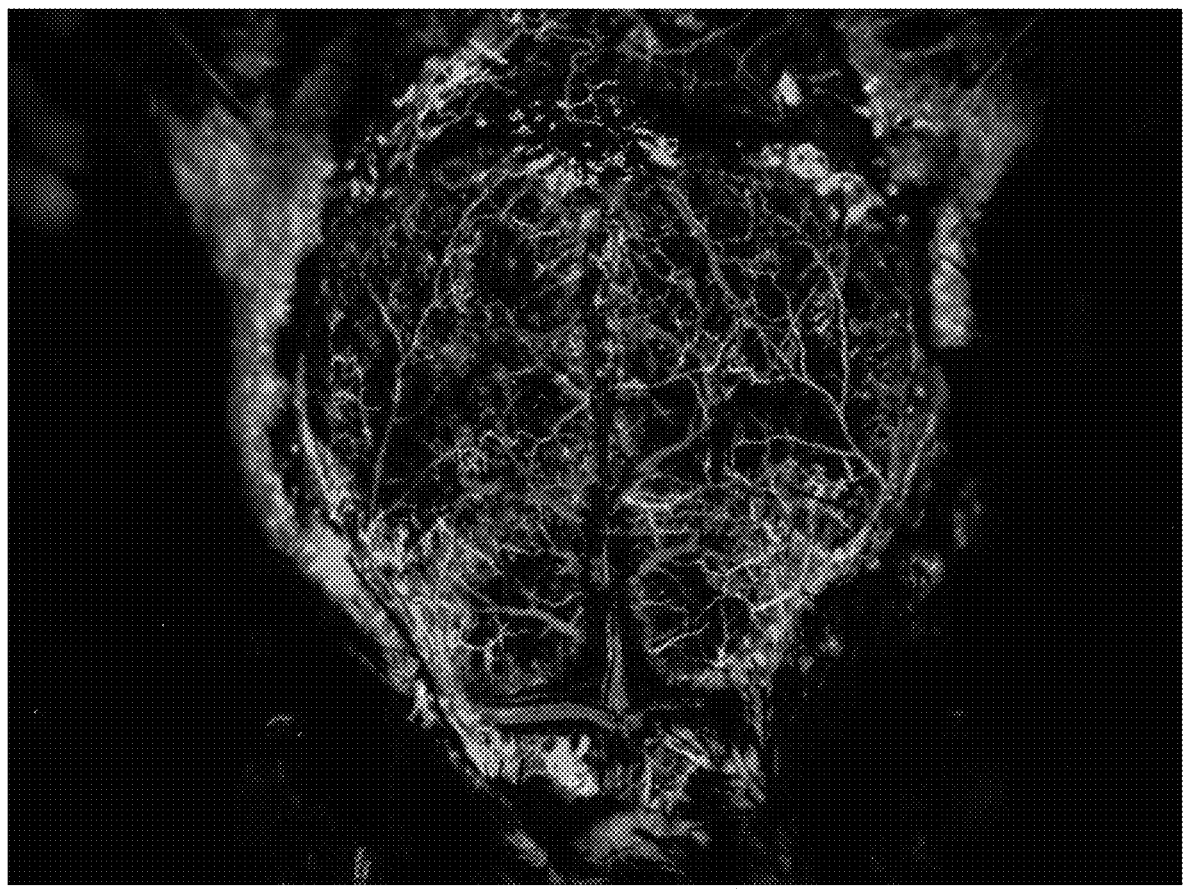
FIG. 21 includes a 3D image computed based on output of a neural network, depicting an improvement in image resolution and/or improvement in differentiation of the bifurcation and/or crossing ambiguity described herein, in accordance with some embodiments of the present invention.

Reference is now made to FIG. 21, which includes a 3D image computed based on output of a neural network (e.g., as described herein and/or neural network 1902 of FIG. 19), depicting an improvement in image resolution and/or improvement in differentiation of the bifurcation and/or crossing ambiguity described herein, in accordance with some embodiments of the present invention.

The image of FIG. 21 is compared to the image shown in FIG. 12 which is computed using other methods, without the neural network. The image of FIG. 21 is processed from images captured of a living mammal, as described with reference to FIG. 12. The image of FIG. 21 is computed using the system set-up as described herein (e.g., with reference to system 200 of FIG. 2, and/or FIG. 5) and processing of the image sequence as described herein (e.g., FIG. 1 and/or FIG. 6 and/or FIG. 19). The local organization of brain vasculature shown in the image of FIG. 21 (which is computed by the neural network) is determined more accurately in comparison to the image of FIG. 12 (which is not computed by the neural network).

Figure 22:
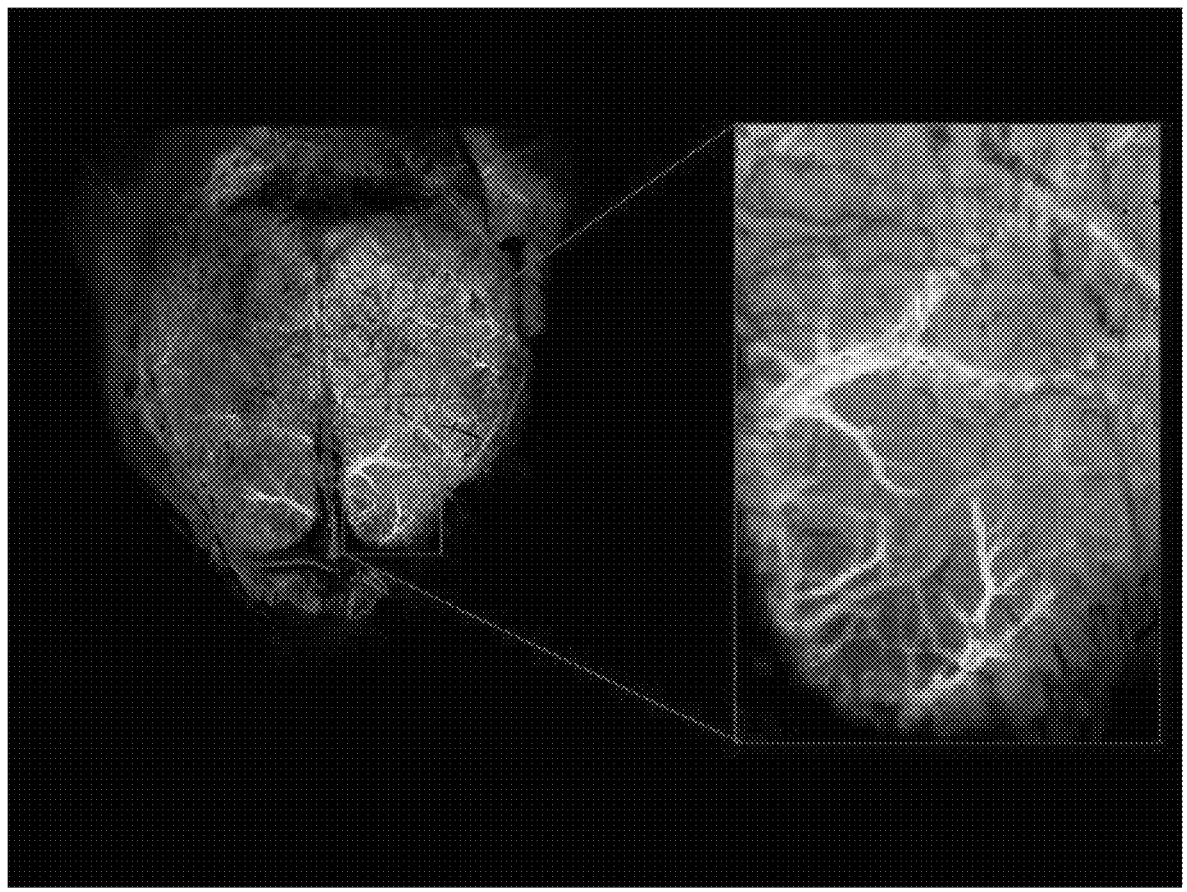
FIG. 22 is a 3D image of a vascular network of the brain computed according to temporal indexation, in accordance with some embodiments of the present invention.

Reference is now made to FIG. 22, which is a 3D image of a vascular network of the brain computed according to the temporal indexation (also referred to herein as time similarity index) described herein (e.g., as described with reference to act 106B of FIG. 1), in accordance with some embodiments of the present invention. As depicted in the image of FIG. 22, the temporal indexation improves resolution for distinguishing substructures of the vein network of the brain. The resolution obtained for the image of FIG. 22 is better than the resolution obtainable using other known methods. As described herein. The temporal indexation enhance the image resolution based on linking together of the pixels associated with common temporal behavior, for example, by taking into account the flow-time delays of the fluorescence circulation (e.g., detecting the more frequent usual patterns, the hidden abnormal structures, and/or normal hidden substructures). Substructures may be color coded according to structure type. The color coding improves distinguishing substructures within the vein network, and linking corresponding structures to achieve a spatial resolution that is better than using existing methods.

It is noted that the performance of the computing unit computing the image is improved based on the increased resolution of the image computed according to the systems, methods, and/or code instruction described herein.

Figure 23:
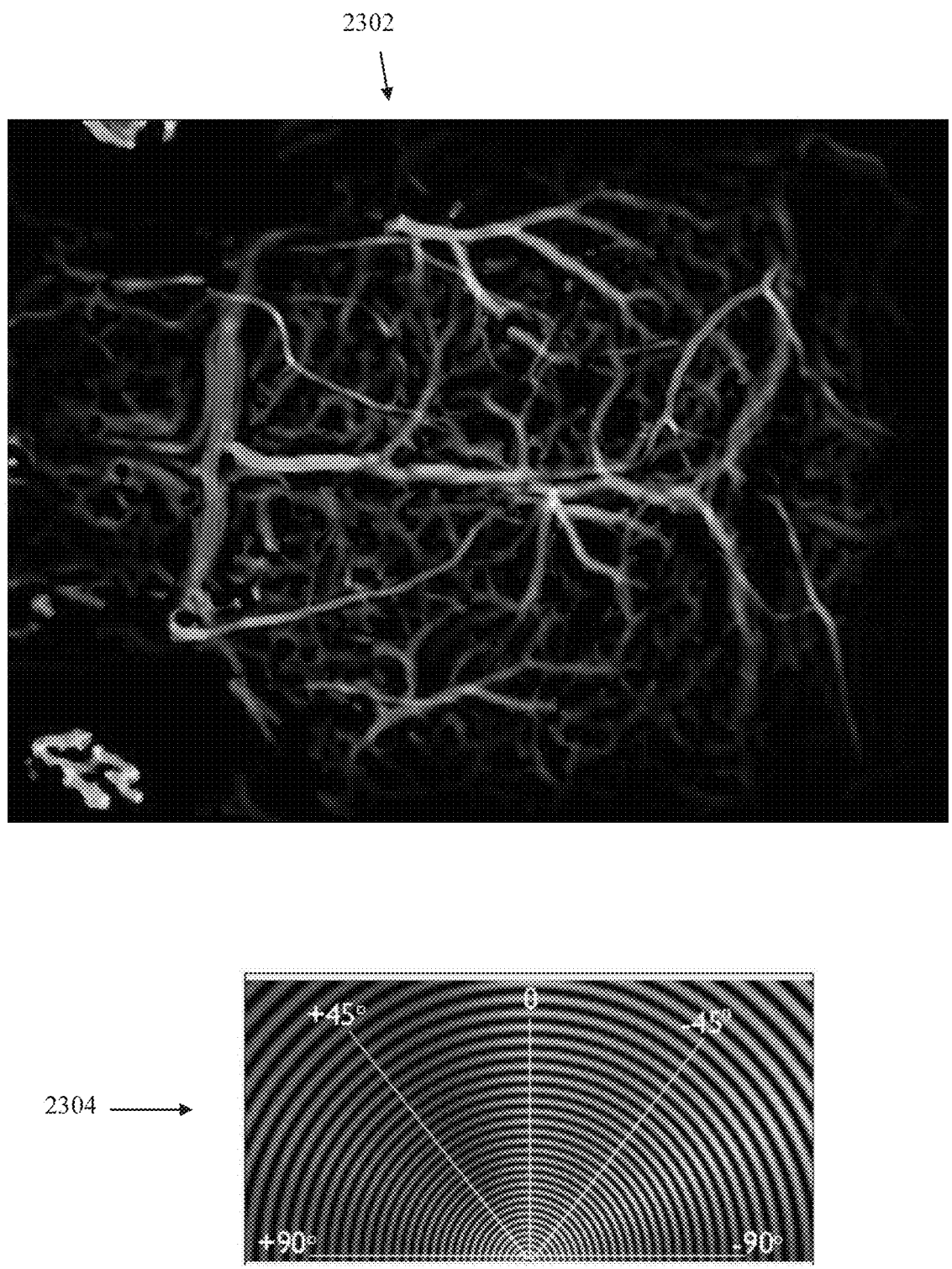
FIG. 23 is an exemplary 3D image of the vascular network of the brain depicting structure tensors, in accordance with some embodiments of the present invention.

Reference is now made to FIG. 23, which is an exemplary 3D image 2302 of the vascular network of the brain depicting orientation structure tensors (e.g., as described with reference to act 106F of FIG. 1), in accordance with some embodiments of the present invention. Image 2302 is computed using the system set-up as described herein (e.g., with reference to system 200 of FIG. 2, and/or FIG. 5) and processing of the image sequence as described herein (e.g., FIG. 1 and/or FIG. 6 and/or FIG. 19). Image 2304 is a wheel orientation defines a mapping between colors of image 2302 and orientation of the computed structure tensors.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant fluorescent illumination agents and imaging sensors will be developed and the scope of the terms fluorescent illumination agent and imaging sensor are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method of generating a three dimensional (3D) image based on fluorescent illumination, comprising:
    receiving in parallel from each of at least three imaging sensors capturing fluorescence illumination and positioned at a respective parallax towards an object having a plurality of regions with fluorescent illumination therein, a respective sequence of a plurality of images including fluorescent illumination of the plurality of regions and depicting scattering of the fluorescent illumination by tissue, each of the plurality of images separated by an interval of time;
    analyzing the respective at least three sequences, to create a volume-dataset indicative of the depth of each respective region of the plurality of regions;
    generating a 3D image according to the volume-dataset; and
    adjusting the 3D image for improved spatial resolution and reduced scatter of the fluorescent illumination by tissue by applying at least one of:
    calculating an isotropic reference;
    computing a deconvolution parameter that compensates for scattering of the fluorescent illumination and estimates diffusion of the fluorescent illumination agent leaking out of vessels; and
    applying an adaptive filter designed to at least one of remove and reduce scattering of the fluorescent illumination, to each respective sequence received by each of the at least three image sensors.

2. The method of claim 1, wherein the object includes tissue within a living mammal, the fluorescent illuminated regions include a plurality of blood vessels injected with fluorescent illumination agent located below the skin of the living mammal, and the at least three imaging sensors are located externally to the skin and non-contacting the skin.

3. The method of claim 1, wherein the analyzing comprises analyzing the respective sequences to compute a respective parallax-dataset for each pair of imaging sensors of the at least three imaging sensors, and computing the volume-dataset based on the respective parallax-dataset of each pair of imaging sensors, wherein the volume-dataset is indicative of the 3D location of each region of the plurality of regions.

4. The method of claim 1, wherein the analyzing comprises computing a time similarity index based on an analysis of at least one pattern indicative of a change of the intensity of the fluorescent illumination at respective image elements of each respective sequence, and computing a type of each of the regions according to the time similarity index.

5. The method of claim 4, wherein the type of each of the regions is computed by linking image elements having a similarity of the at least one pattern indicative of the change of intensity of the fluorescent illumination, wherein the similarity is defined according to a similarity requirement based on the time similarity index.

6. The method according to claim 5, wherein the similarity requirement is computed according to the equation:

$$S_i = \left[\frac{\text{Max}[I_r^2(t)]}{\delta_d}\right]^{1/3}$$

Where:

Ir(t) denotes a reference temporal function,

Si denotes a temporal assessment that defines relative distance between Ic(t) denoting a current temporal function, by comparison with Ir(t)

$$\delta_d = \sum_{t=0}^{T} \frac{|I_c(t) - I_r(t)|}{I_c(t) + I_r(t)},$$

and the similarity is computed as a Manhattan distance according to the relationship |Ic(t)-Ir(t)|.

7. The method of claim 5, wherein the at least one pattern indicative of the change in the intensity of the fluorescent illumination comprises at least one of: time to maximum intensity of the fluorescent illumination and approximately stable intensity of the fluorescent illumination over a time interval.

8. The method of claim 5, wherein a neural network receives the respective sequences and computes the time similarity index, to output the volume-dataset indicative of the depth of each respective region of the plurality of regions.

9. The method of claim 1, further comprising calculating said isotropic reference, and improving spatial resolution of the generated 3D image according to the isotropic reference.

10. The method of claim 1, further comprising calculating a spatio-temporal distortion compensation matrix (STDCM) that includes weighted coefficients, and applying the STDCM to the volume-dataset to correct the depth coordinates of each image element of each region; wherein the STDCM is computed based on a plurality of computed time shape index parameters associated with at least one pattern of fluorescent intensity over time at each respective image element, computed based on the respective sequences, wherein the plurality of computed time shape index parameters are used to resolve structure and/or function details of the volume-dataset.

11. The method of claim 10, wherein the plurality of computed time shape index parameters used to resolve structure and/or function details are selected from the group consisting of: fine structural details, type of blood vessel, topology indicating a bifurcation of a vessel or crossing over of vessels, blood vessel classification, fluorescent contrast extravasation, and normal functional state or abnormal behavior.

12. The method of claim 1, further comprising calculating a motion estimator based on an analysis of changes in intensity of the fluorescent illumination of the image elements of the respective sequences, and applying the motion estimator to the volume-dataset to correct motion artifacts.

13. The method of claim 1, further comprising computing said deconvolution parameter that compensates for scattering of the fluorescent illumination and estimates diffusion of the fluorescent illumination agent leaking out of vessels, the deconvolution parameter used to correct the volume-dataset and improve spatial resolution of the plurality of regions.

14. The method of claim 1, further comprising computing structure tensors based on the respective parallax shift of at least three imaging sensors, and computing the volume-dataset according to the structure tensors for improving the depth and/or parallax sensitivity of the plurality of regions within the 3D image.

15. The method of claim 1, wherein the analyzing the respective sequences is performed using a trained time similarity index classifier that receives as input a computed initial location of each respective image element according to respective sequences of the at least three image sensors, and at least one pattern of changes in fluorescent imaging at each respective image element, and outputs the volume-dataset based on a computed maximum correlation of the location of each respective image element.

16. The method of claim 1, further comprising applying said adaptive filter to each respective sequence received by each of the at least three image sensors, the adaptive filter designed to improve spatial resolution of the location of each region and to reduce noise during variations in intensity of the fluorescent illumination.

17. The method of claim 1, further comprising applying the adaptive filter to each respective sequence received by each of the at least three image sensors, the adaptive filter designed to remove scattering effect of media of the object, wherein the adaptive filter is implemented as a super-Gaussian background subtraction by subtracting the adaptive filter from each image of the plurality of image of each sequence.

18. A system for generating a three dimensional (3D) image based on fluorescent illumination, comprising:
an imaging interface that receives in parallel from each of at least three imaging sensors capturing fluorescence illumination and positioned at a respective parallax towards an object having a plurality of regions with fluorescent illumination therein, a respective sequence of a plurality of images including fluorescent illumination of the plurality of regions depicting scattering of the fluorescent illumination by tissue, each of the plurality of images separated by an interval of time;
a program store storing code; and
at least one processor coupled to the imaging interface and the program store for implementing the stored code, the code comprising:
code to analyze the respective at least three sequences, create a volume-dataset indicative of the depth of each respective region of the plurality of regions, generate a 3D image according to the volume-dataset, and adjust the 3D image for improved spatial resolution and reduced scatter of the fluorescent illumination by tissue by applying at least one of:
calculating an isotropic reference;
computing a deconvolution parameter that compensates for scattering of the fluorescent illumination and estimates diffusion of the fluorescent illumination agent leaking out of vessels; and
applying an adaptive filter designed to at least one of remove and reduce scattering of the fluorescent illumination, to each respective sequence received by each of the at least three image sensors.

19. The system of claim 18, further comprising a laser and another imaging sensor positioned at the center of the at least three imaging sensors, and code instructions stored by the program store, the code comprising code to analyze the images created based on reflections of the laser captured by the another imaging sensor to compute laser speckle imaging (LSI), and generate the 3D image in real-time based on the volume-dataset using the LSI as an independent reference.

20. A computer program product comprising a non-transitory computer readable storage medium storing program code thereon for implementation by at least one processor, for generating a three dimensional (3D) image based on fluorescent illumination, comprising:

code instructions to receive in parallel from each of at least three imaging sensors capturing fluorescence illumination and positioned at a respective parallax towards an object having a plurality of regions with fluorescent illumination therein, a respective sequence of a plurality of images including fluorescent illumination of the plurality of regions depicting scattering of the fluorescent illumination by tissue, each of the plurality of images separated by an interval of time;

code instructions to analyze the respective at least three sequences, to create a volume-dataset indicative of the depth of each respective region of the plurality of regions;

code instructions to generate a 3D image according to the volume-dataset; and code instructions to adjust the 3D image for improved spatial resolution and reduced scatter of the fluorescent illumination by tissue by applying at least one of:
calculating an isotropic reference;
computing a deconvolution parameter that compensates for scattering of the fluorescent illumination and estimates diffusion of the fluorescent illumination agent leaking out of vessels; and
applying an adaptive filter designed to at least one of remove and reduce scattering of the fluorescent illumination, to each respective sequence received by each of the at least three image sensors.

21. The method of claim 4, further comprising using the computed time similarity index to localize a scattering precursor before propagation of the fluorescent light through tissue.

* * * * *